United States Patent
Tanaka et al.

(10) Patent No.: US 10,899,912 B2
(45) Date of Patent: Jan. 26, 2021

(54) RESIN COMPOSITION AND RESIN MOLDED ARTICLE

(71) Applicant: Eastman Chemical Company, Kingsport, TN (US)

(72) Inventors: Ryo Tanaka, Minamiashigara (JP); Kana Miyazaki, Minamiashigara (JP); Kenji Yao, Minamiashigara (JP)

(73) Assignee: Eastman Chemical Company, Kingsport, TN (US)

( * ) Notice: Subject to any disclaimer, the term of this patent is extended or adjusted under 35 U.S.C. 154(b) by 0 days.

(21) Appl. No.: 16/245,874

(22) Filed: Jan. 11, 2019

(65) Prior Publication Data
US 2020/0071494 A1   Mar. 5, 2020

(30) Foreign Application Priority Data
Aug. 31, 2018   (JP) ................ 2018-164064

(51) Int. Cl.
| | | |
|---|---|---|
| *C08L 1/14* | (2006.01) | |
| *C08K 5/13* | (2006.01) | |
| *C08K 5/524* | (2006.01) | |
| *C07D 311/74* | (2006.01) | |
| *B29C 45/00* | (2006.01) | |
| *C08K 5/17* | (2006.01) | |
| *B29K 1/00* | (2006.01) | |

(52) U.S. Cl.
CPC .......... *C08L 1/14* (2013.01); *B29C 45/0001* (2013.01); *C07D 311/74* (2013.01); *C08K 5/13* (2013.01); *C08K 5/17* (2013.01); *C08K 5/524* (2013.01); *B29K 2001/08* (2013.01)

(58) Field of Classification Search
None
See application file for complete search history.

(56) References Cited

U.S. PATENT DOCUMENTS

| | | |
|---|---|---|
| 2016/0090473 A1 | 3/2016 | Yao et al. |
| 2017/0081505 A1 | 3/2017 | Yao et al. |

FOREIGN PATENT DOCUMENTS

| | | |
|---|---|---|
| JP | 2016-069423 A | 5/2016 |
| JP | 2019-151796 A | 9/2019 |
| JP | 2019-151797 A | 9/2019 |

OTHER PUBLICATIONS

Toyama, Cellulose (2015) 22:1625-1639. (Year: 2015).*

* cited by examiner

*Primary Examiner* — Layla D Berry
(74) *Attorney, Agent, or Firm* — Robert C. Morriss

(57) ABSTRACT

A resin composition is provided and includes: a cellulose acylate (A); a cardanol compound (B); and a compound (C), and the compound (C) is at least one selected from the group consisting of a hindered phenol compound, a tocopherol compound, a tocotrienol compound, a phosphite compound, and a hydroxylamine compound.

15 Claims, No Drawings

RESIN COMPOSITION AND RESIN MOLDED ARTICLE

CROSS-REFERENCE TO RELATED APPLICATIONS

This application is based on and claims a priority under 35 USC 119 from Japanese Patent Application No. 2018-164064 filed on Aug. 31, 2018.

BACKGROUND

Technical Field

The present invention relates to a resin composition and a resin molded article.

Related Art

JP-A-2016-069423 discloses a resin composition containing a cellulose ester resin, a compound containing an adipate ester, and a polyhydroxyalkanoate resin.

SUMMARY

Aspects of certain non-limiting embodiments of the present disclosure relate to a resin composition, from which a resin molded article excellent in toughness may be obtained, compared with a resin composition containing a cellulose acylate (A) and a cardanol compound (B), and not containing compound (C) which is a hindered phenol compound, a tocopherol compound, a tocotrienol compound, a phosphite compound, or a hydroxylamine compound, and containing a hindered amine compound.

Aspects of certain non-limiting embodiments of the present disclosure address the above advantages and/or other advantages not described above. However, aspects of the non-limiting embodiments are not required to address the advantages described above, and aspects of the non-limiting embodiments of the present disclosure may not address advantages described above.

According to an aspect of the present disclosure, there is provided a resin composition, including:
a cellulose acylate (A);
a cardanol compound (B); and
a compound (C) being at least one selected from the group consisting of a hindered phenol compound, a tocopherol compound, a tocotrienol compound, a phosphite compound, and a hydroxylamine compound.

DETAILED DESCRIPTION

Hereinafter, exemplary embodiments of the present disclosure are described. These descriptions and examples are illustrative of the exemplary embodiments and do not limit the scope of the exemplary embodiments.

In the present disclosure, a numerical value indicated by using "to" indicates a range including the numerical values described before and after "to" as the minimum value and the maximum value, respectively.

In the numerical ranges described in the present disclosure in stages, the upper limit value or the lower limit value described in one numerical range may be replaced by the upper limit value or the lower limit value of the numerical range of another numerical range. In addition, in the numerical range described in the present disclosure, the upper limit value or the lower limit value of the numerical range may be replaced by the values shown in the examples.

In the present disclosure, the term "step" include not only an independent step but also a step as long as the intended purpose of the step is achieved even when the step may not be clearly distinguished from other steps.

In the present disclosure, each component may contain a plurality of corresponding substances. In the present disclosure, in a case of referring to the amount of each component in a composition, it means the total amount of a plurality of kinds of substances present in the composition when there are the plurality of kinds of substances corresponding to each component in the composition, unless otherwise specified.

In the present disclosure, "(meth)acryl" means at least one of acryl and methacryl, and "(meth)acrylate" means at least one of acrylate and methacrylate.

In the present disclosure, the cellulose acylate (A), the cardanol compound (B), the compound (C) and the thermoplastic elastomer (D) are also referred to as component (A), component (B), component (C) and component (D), respectively.

<Resin Composition>

A resin composition according to the exemplary embodiment contains a cellulose acylate (A), a cardanol compound (B), and a compound (C) being at least one selected from the group consisting of a hindered phenol compound, a tocopherol compound, a tocotrienol compound, a phosphite compound, and a hydroxylamine compound.

According to the resin composition of the exemplary embodiment, a resin molded article excellent in toughness is obtained. The toughness in the present disclosure is a performance evaluated by impact absorption energy (unit: J) obtained by a puncture impact test. A Charpy impact strength in the present disclosure is a performance evaluated by a Charpy impact strength (unit: $kJ/m^2$).

As a result of an investigation by the present inventors, it is found that a resin molded article obtained from a resin composition containing a cellulose acylate (A) and a cardanol compound (B) acting as a plasticizer to the cellulose acylate (A) and not containing a compound (C) is excellent in Charpy impact strength, but not high in toughness for the Charpy impact strength. For example, when comparing Comparative Example 1 (a resin composition containing the cellulose acylate (A) and the cardanol compound (B) without the compound (C)) with Reference Example A (a resin composition containing the cellulose acylate (A) and an adipate ester which is a different plasticizer from the cardanol compound (B) without the compound (C)), which are to be descried later, there is no great difference between the Charpy impact strengths of the two resin compositions, but the impact absorption energy of Comparative Example 1 is significantly lower than the impact absorption energy of Reference Example A. That is, the resin molded article obtained from the resin composition containing the cellulose acylate (A) and the cardanol compound (B) is not high in toughness in spite of the excellent Charpy impact strength thereof.

As a result of a further investigation by the present inventors, it is found that when the compound (C) is added to the resin composition containing the cellulose acylate (A) and the cardanol compound (B), the toughness is higher than that of a resin composition without the addition of the compound (C). The following mechanism may be considered as a mechanism for improving the toughness of the resin molded article by adding the compound (C).

When the resin composition containing the cellulose acylate (A) and the cardanol compound (B) is thermally processed to produce a resin molded article, it is presumed that a side chain of the cellulose acylate (A) is eliminated to generate a carboxylic acid, the resin composition is in an acidic state, and the cardanol compound (B) is oxidized. It is presumed that the oxidized cardanol compound (B) more easily aligns a molecular orientation of the cellulose acylate (A) than an unoxidized cardanol compound (B), and the molecular orientation of the cellulose acylate (A) in the resin molded article is aligned. Then, it is presumed that the resin molded article is easy to cause brittle fracture along the molecular orientation of the cellulose acylate (A), and thus the toughness is not high in spite of the high Charpy impact strength.

In contrast, when the compound (C) is added to the resin composition, and the resin composition is thermally processed to produce a resin molded article, it is presumed that the compound (C) suppresses the generation of a carboxylic acid from the cellulose acylate (A) or the oxidation of the cardanol compound (B). It is presumed that since the unoxidized cardanol compound (B) does not show an effect of aligning the molecular orientation of the cellulose acylate (A) to induce the brittle fracture, the toughness of the resin molded article is not impaired, and the resin molded article is improved due to a correlation with the Charpy impact strength.

In the related art, the compound (C) is used as an oxidation inhibitor or a stabilizer in a resin composition. As a result of an investigation by the present inventors, it is found that even when another chemical substance (e.g., a hindered amine compound) known as an oxidation inhibitor or a stabilizer is added to the resin composition containing the cellulose acylate (A) and the cardanol compound (B) instead of the compound (C), an effect of improving the toughness may not be obtained (shown in Comparative Example 6 and Comparative Example 12 to be described later). Although the detailed mechanism is unknown, it is presumed that a mechanism other than inhibiting the generation of the carboxylic acid from the cellulose acylate (A) or the oxidation of the cardanol compound (B) also works for the compound (C) to improve the toughness of the resin molded article.

In contrast, as can be seen from a comparison between Reference Example A and Reference Example B, which are to be described later, even when the compound (C) is added to the resin composition containing the cellulose acylate (A) and the adipate ester, no improvement in toughness of the resin molded article is observed.

It is presumed from the above that the compound (C) does not always develop the effect of improving the toughness of the resin molded article in any resin compositions, but the compound (C) may develop the effect of improving the toughness of the resin molded article in combination of the cellulose acylate (A), the cardanol compound (B), and the compound (C).

From the viewpoint of further improving the toughness or the Charpy impact strength of the resin molded article, it is preferable that the resin composition according to the exemplary embodiment further contains a thermoplastic elastomer (D).

Hereinafter, components of the resin composition according to the exemplary embodiment are described in detail.

[Cellulose Acylate (A): Component (A)]

The cellulose acylate (A) is a cellulose derivative in which at least a part of hydroxy groups in a cellulose are substituted (acylated) with an acyl group. The acyl group is a group having a structure of —CO—$R^{AC}$ ($R^{AC}$ represents a hydrogen atom or a hydrocarbon group).

The cellulose acylate (A) is, for example, a cellulose derivative represented by the following General Formula (CA).

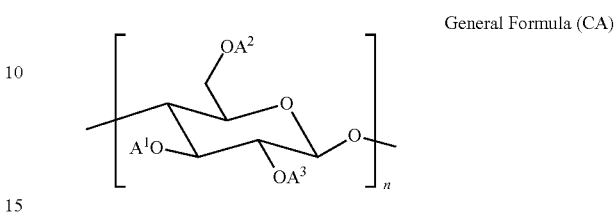

General Formula (CA)

In the General Formula (CA), $A^1$, $A^2$ and $A^3$ each independently represent a hydrogen atom or an acyl group, and n represents an integer of 2 or more. However, at least a part of n $A^1$, n $A^2$ and n $A^3$ represents an acyl group. All of n $A^1$ in the molecule may be the same, partly the same or different from each other. Similarly, all of n $A^2$ and n $A^3$ in the molecule may be the same, partly the same or different from each other.

The hydrocarbon group in the acyl group represented by $A^1$, $A^2$ and $A^3$ may be linear, branched or cyclic, and is preferably linear or branched, and more preferably linear.

The hydrocarbon group in the acyl group represented by $A^1$, $A^2$ and $A^3$ may be a saturated hydrocarbon group or an unsaturated hydrocarbon group, and more preferably a saturated hydrocarbon group.

The acyl group represented by $A^1$, $A^2$ and $A^3$ is preferably an acyl group having 1 to 6 carbon atoms. That is, the cellulose acylate (A) preferably has an acyl group with 1 to 6 carbon atoms. A resin molded article excellent in impact resistance may be more easily obtained from the cellulose acylate (A) having an acyl group with 1 to 6 carbon atoms, than a cellulose acylate (A) having an acyl group with 7 or more carbon atoms.

The acyl group represented by $A^1$, $A^2$ and $A^3$ may be a group in which a hydrogen atom in the acyl group is substituted with a halogen atom (e.g., a fluorine atom, a bromine atom and an iodine atom), an oxygen atom, a nitrogen atom or the like, and is preferably unsubstituted.

Examples of the acyl group represented by $A^1$, $A^2$ and $A^3$ include a formyl group, an acetyl group, a propionyl group, a butyryl group (a butanoyl group), a propenoyl group, a hexanoyl group. Of these, as the acyl group, an acyl group having 2 to 4 carbon atoms is preferred, and an acyl group having 2 or 3 carbon atoms is more preferred, from the viewpoint of obtaining a moldability of the resin composition, an impact resistance of the resin molded article or the excellent toughness of the resin molded article.

Examples of the cellulose acylate (A) include a cellulose acetate (cellulose monoacetate, cellulose diacetate (DAC), and cellulose triacetate), a cellulose acetate propionate (CAP), and a cellulose acetate butyrate (CAB).

As the cellulose acylate (A), a cellulose acetate propionate (CAP) and a cellulose acetate butyrate (CAB) are preferred, and a cellulose acetate propionate (CAP) is more preferred from the viewpoint of obtaining the impact resistance of the resin molded article or the excellent toughness of the resin molded article.

The cellulose acylate (A) may be used alone, or may be used in combination of two or more thereof.

The cellulose acylate (A) preferably has a weight-average degree of polymerization of 200 to 1000, more preferably 500 to 1000, and still more preferably 600 to 1000 from the viewpoint of obtaining the moldability of the resin composition, the impact resistance of the resin molded article or the excellent toughness of the resin molded article.

The weight-average degree of polymerization of the cellulose acylate (A) is determined from a weight average molecular weight (Mw) of the cellulose acylate (A) by the following procedures.

First, the weight average molecular weight (Mw) of the cellulose acylate (A) is measured in terms of polystyrene by a gel permeation chromatography apparatus (GPC apparatus: HLC-8320 GPC manufactured by Tosoh Corporation, column: TSK gel α-M) using tetrahydrofuran.

Subsequently, a degree of polymerization of the cellulose acylate (A) is determined by dividing by a structural unit molecular weight of the cellulose acylate (A). For example, in a case where the substituent of the cellulose acylate is an acetyl group, the structural unit molecular weight of the cellulose acylate (A) is 263 when the degree of substitution is 2.4 and the structural unit molecular weight of the cellulose acylate (A) is 284 when the degree of substitution is 2.9.

The cellulose acylate (A) preferably has a degree of substitution of 2.1 to 2.9, more preferably 2.2 to 2.9, still more preferably 2.3 to 2.9, and particularly preferably 2.6 to 2.9, from the viewpoint of obtaining the moldability of the resin composition, the impact resistance of the resin molded article or the excellent toughness of the resin molded article.

In the cellulose acetate propionate (CAP), a ratio of the degrees of substitution of the acetyl group to the propionyl group (acetyl group/propionyl group) is preferably 0.01 to 1, and more preferably 0.05 to 0.1, from the viewpoint of obtaining the moldability of the resin composition, the impact resistance of the resin molded article or the excellent toughness of the resin molded article.

As the CAP, a CAP satisfying at least one of the following (1), (2), (3) and (4) is preferred, a CAP satisfying the following (1), (3) and (4) is more preferred, and a CAP satisfying the following (2), (3) and (4) is still more preferred. (1) When measured by the GPC method using tetrahydrofuran as a solvent, the weight average molecular weight (Mw) in terms of polystyrene is 160,000 to 250,000, and a ratio Mn/Mz of a number average molecular weight (Mn) in terms of polystyrene to a Z average molecular weight (Mz) in terms of polystyrene is 0.14 to 0.21. (2) When measured by the GPC method using tetrahydrofuran as a solvent, the weight average molecular weight (Mw) in terms of polystyrene is 160,000 to 250,000, a ratio Mn/Mz of a number average molecular weight (Mn) in terms of polystyrene to a Z average molecular weight (Mz) in terms of polystyrene is 0.14 to 0.21, and a ratio Mw/Mz of a weight average molecular weight (Mw) in terms of polystyrene to the Z average molecular weight (Mz) in terms of polystyrene is 0.3 to 0.7. (3) When measured by a Capirograph at a condition of 230° C. according to ISO 11443: 1995, a ratio $\eta1/\eta2$ of a viscosity $\eta1$ (Pa·s) at a shear rate of 1216 (/sec) to a viscosity $\eta2$ (Pa·s) at a shear rate of 121.6 (/sec) is 0.1 to 0.3. (4) When a small square plate test piece (D11 test piece specified by JIS K7139:2009, 60 mm×60 mm, thickness 1 mm) obtained by an injection molding of the CAP is allowed to stand in an atmosphere at a temperature of 65° C. and a relative humidity of 85% for 48 hours, both an expansion coefficient in an MD direction and an expansion coefficient in a TD direction are 0.4% to 0.6%. Here, the MD direction means a length direction of a cavity of a mold used for the injection molding, and the TD direction means a direction orthogonal to the MD direction.

In the cellulose acetate butyrate (CAB), a ratio of degrees of substitution of the acetyl group to the butyryl group (acetyl group/butyryl group) is preferably 0.05 to 3.5, and more preferably 0.5 to 3.0, from the viewpoint of obtaining the moldability of the resin composition, the impact resistance of the resin molded article or the excellent toughness of the resin molded article.

The degree of substitution of the cellulose acylate (A) is an index indicating a degree to which the hydroxy group of the cellulose is substituted with the acyl group. That is, the degree of substitution is an index indicating a degree of acylation of the cellulose acylate (A). Specifically, the degree of substitution means an intramolecular average of the number of substitution in which three hydroxy groups in a D-glucopyranose unit of the cellulose acylate (A) are substituted with the acyl group. The degree of substitution is determined from a ratio of a peak integral of a cellulose-derived hydrogen to a peak integral of an acyl group-derived hydrogen with $^1$H-NMR (JMN-ECA, manufactured by JEOL RESONANCE Co., Ltd.).

[Cardanol Compound (B): Component (B)]

The cardanol compound refers to a component (e.g., a compound represented by the following structural formulas (b-1) to (b-4)) contained in a compound naturally derived from cashews or a derivative derived from the above component.

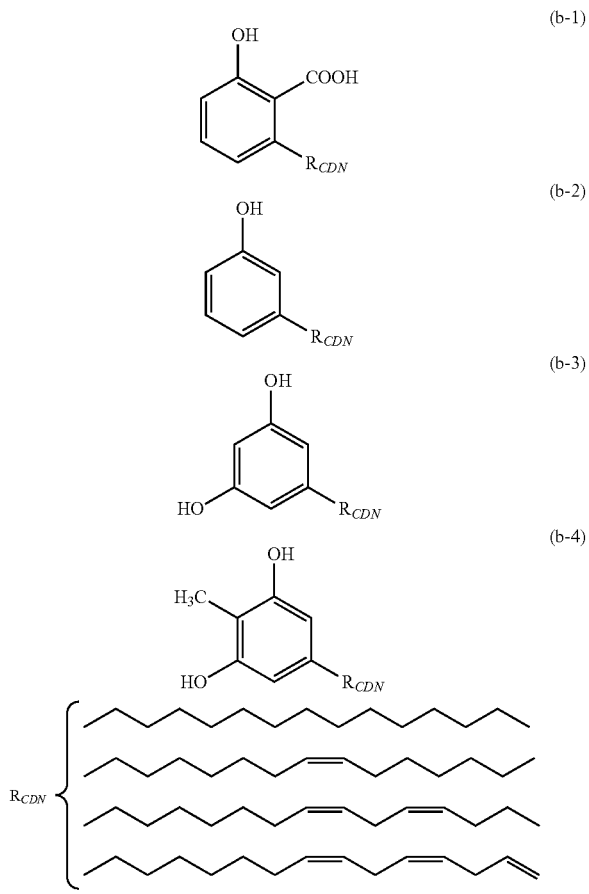

The resin composition according to the exemplary embodiment may contain, as the cardanol compound (B), a mixture of compounds naturally derived from cashews (hereinafter also referred to as "cashew-derived mixture").

The resin composition according to the exemplary embodiment may contain a derivative from the cashew-derived mixture as the cardanol compound (B). Examples of the derivative from the cashew-derived mixture include the following mixtures, and monomers.

Mixture prepared by adjusting a composition ratio of each component in the cashew-derived mixture Monomer obtained by isolating only a specific component from the cashew-derived mixture Mixture containing a modified product obtained by modifying a component in the cashew-derived mixture Mixture containing a polymer obtained by polymerizing a component in the cashew-derived mixture Mixture containing a modified polymer obtained by modifying and polymerizing a component in the cashew-derived mixture Mixture containing a modified product obtained by further modifying a component in the mixture whose composition ratio is adjusted Mixture containing a polymer obtained by further polymerizing a component in the mixture whose composition ratio is adjusted Mixture containing a modified polymer obtained by further modifying and polymerizing a component in the mixture whose composition ratio is adjusted Modified product obtained by further modifying the isolated monomer Polymer obtained by further polymerizing the isolated monomer Modified polymer obtained by further modifying and polymerizing the isolated monomer Here, the monomer includes a multimer such as a dimer and a trimer.

The cardanol compound (B) is preferably a compound being at least one selected from the group consisting of a compound represented by a General Formula (CDN1) and a polymer obtained by polymerizing a compound represented by the General Formula (CDN1), from the viewpoint of obtaining the impact resistance of the resin molded article.

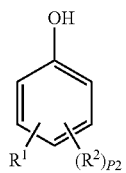

General Formula (CDN1)

In the General Formula (CDN1), $R^1$ represents an alkyl group optionally having a substituent, or an unsaturated aliphatic group optionally having a double bond and a substituent. $R^2$ represents a hydroxy group, a carboxy group, an alkyl group optionally having a substituent, or an unsaturated aliphatic group optionally having a double bond and a substituent. P2 represents an integer of 0 to 4. When P2 is 2 or more, a plurality of $R^2$ may be the same group or different groups.

In the General Formula (CDN1), the alkyl group optionally having a substituent represented by $R^1$ is preferably an alkyl group having 3 to 30 carbon atoms, more preferably an alkyl group having 5 to 25 carbon atoms, and still more preferably an alkyl group having 8 to 20 carbon atoms.

Examples of the substituent contained in the alkyl group include: a hydroxy group; a substituent containing an ether bond, such as an epoxy group or a methoxy group; a substituent containing an ester bond, such as an acetyl group or a propionyl group; or the like.

Examples of the alkyl group optionally having a substituent include pentadecan-1-yl, heptan-1-yl, octan-1-yl, nonan-1-yl, decan-1-yl, undecan-1-yl, dodecan-1-yl, tetradecan-1-yl, or the like.

In the General Formula (CDN1), the unsaturated aliphatic group optionally having a double bond and a substituent represented by le is preferably an unsaturated aliphatic group having 3 to 30 carbon atoms, more preferably an unsaturated aliphatic group having 5 to 25 carbon atoms, and still more preferably an unsaturated aliphatic group having 8 to 20 carbon atoms.

The number of the double bond contained in the unsaturated aliphatic group is preferably 1 to 3.

Examples of the substituent contained in the unsaturated aliphatic group include those listed as the substituent of the alkyl group.

Examples of the unsaturated aliphatic group optionally having a double bond and a sub stituent include pentadeca-8-en-1-yl, pentadeca-8,11-dien-1-yl, pentadeca-8,11,14-trien-1-yl, pentadeca-7-en-1-yl, pentadeca-7,10-dien-1-yl, pentadeca-7,10,14-trien-1-yl, or the like.

In the General Formula (CDN1), $R^1$ is preferably pentadeca-8-en-1-yl, pentadeca-8,11-dien-1-yl, pentadeca-8,11,14-trien-1-yl, pentadeca-7-en-1-yl, pentadeca-7,10-dien-1-yl, and pentadeca-7,10,14-trien-1-yl.

In the General Formula (CDN1), preferred examples of the alkyl group optionally having a substituent and the unsaturated aliphatic group optionally having a double bond and a substituent, which are represented by $R^2$, include those listed as the alkyl group optionally having a substituent and the unsaturated aliphatic group optionally having a double bond and a substituent, which are represented by $R^1$.

The compound represented by the General Formula (CDN1) may be further modified. For example, the compound may be epoxidized. Specifically, the compound may be a compound having a structure in which the hydroxy group of the compound represented by the General Formula (CDN1) is replaced with the following group (EP), i.e., a compound represented by the following General Formula (CDN1-e).

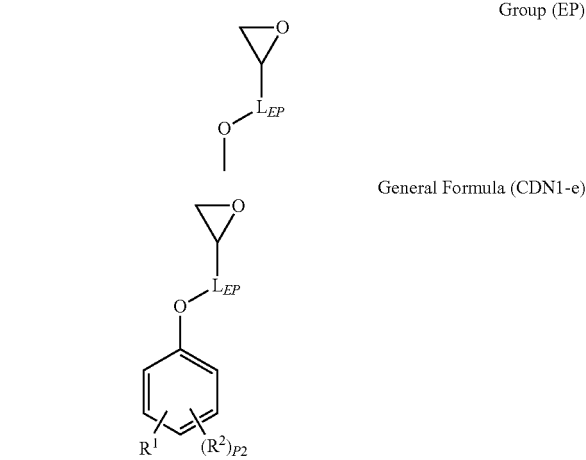

In the group (EP) and the General Formula (CDN1-e), $L_{EP}$ represents a single bond or a divalent linking group. In the General Formula (CDN1-e), $R^1$, $R^2$ and P2 each independently have the same meanings as R', $R^2$ and P2 in the General Formula (CDN1).

In the group (EP) and the General Formula (CDN1-e), examples of the divalent linking group represented by $L_{EP}$ include an alkylene group optionally having a substituent (preferably an alkylene group having 1 to 4 carbon atoms, and more preferably an alkylene group having 1 carbon atom), —$CH_2CH_2OCH_2CH_2$—, or the like.

Examples of the substituent contained in the alkylene group include those listed as the substituent for le of the General Formula (CDN1).

$L_{EP}$ is preferably a methylene group.

The polymer obtained by polymerizing a compound represented by the General Formula (CDN1) refers to a polymer obtained by polymerizing at least two compounds represented by the General Formula (CDN1) with or without a linking group.

Examples of the polymer obtained by polymerizing the compound represented by the General Formula (CDN1) include a compound represented by the following General Formula (CDN2).

General Formula (CDN2)

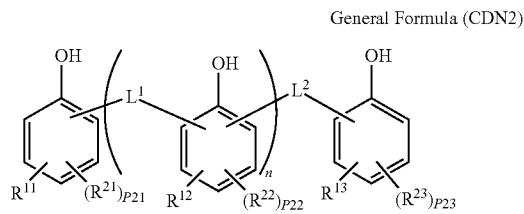

In the General Formula (CDN2), $R^{11}$, $R^{12}$ and $R^{13}$ each independently represent an alkyl group optionally having a substituent, or an unsaturated aliphatic group optionally having a double bond and a substituent. $R^{21}$, $R^{22}$ and $R^{23}$ each independently represent a hydroxy group, a carboxy group, an alkyl group optionally having a substituent, or an unsaturated aliphatic group optionally having a double bond and a substituent. P21 and P23 each independently represent an integer of 0 to 3, and P22 represents an integer of 0 to 2. $L^1$ and $L^2$ each independently represent a divalent linking group. n represents an integer of 0 to 10. A plurality of $R^{21}$ existing when P21 is 2 or more may be the same group or different groups, a plurality of $R^{22}$ existing when P22 is 2 or more may be the same group or different groups, and a plurality of $R^{23}$ existing when P23 is 2 or more may be the same group or different groups. A plurality of $R^{12}$ existing when n is 2 or more may be the same group or different groups, a plurality of $R^{22}$ existing when n is 2 or more may be the same group or different groups, a plurality of $L^1$ existing when n is 2 or more may be the same group or different groups, and a plurality of P22 existing when n is 2 or more may be the same number or different numbers.

In the General Formula (CDN2), preferred examples of the alkyl group optionally having a substituent, and the unsaturated aliphatic group optionally having a double bond and a substituent, which are represented by $R^{11}$, $R^{12}$, $R^{13}$, $R^{21}$, $R^{22}$ and include those listed as $R^1$ of the General Formula (CDN1).

In the General Formula (CDN2), examples of the divalent linking group represented by $L^1$ and $L^2$ include an alkylene group optionally having a substituent (preferably an alkylene group having 2 to 30 carbon atoms, and more preferably an alkylene group having 5 to 20 carbon atoms), or the like.

Examples of the substituent contained in the alkylene group include those listed as the substituent for $R^1$ of the General Formula (CDN1).

In the General Formula (CDN2), n is preferably 1 to 10, and more preferably 1 to 5.

The compound represented by the General Formula (CDN2) may be further modified. For example, the compound may be epoxidized. Specifically, the compound may be a compound having a structure in which the hydroxy group of the compound represented by the General Formula (CDN2) is replaced with the group (EP), i.e., a compound represented by the following General Formula (CDN2-e).

General Formula (CDN2-e)

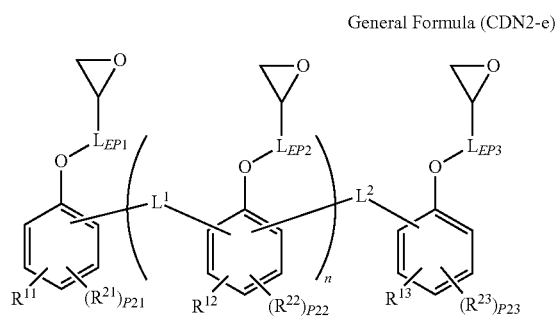

In the General Formula (CDN2-e), $R^{11}$, $R^{12}$, $R^{13}$, $R^{21}$, $R^{22}$, $R^{23}$, P21, P22, P23, $L^1$, $L^2$ and n each have the same meaning as $R^{11}$, $R^{12}$, $R^{13}$, $R^{21}$, $R^{22}$, $R^{23}$, P21, P22, P23, $L^1$, $L^2$ and n in the General Formula (CDN2), respectively.

In the General Formula (CDN2-e), $L_{EP1}$, $L_{EP2}$ and $L_{EP3}$ each independently represent a single bond or a divalent linking group. When n is 2 or more, a plurality of $L_{EP2}$ may be the same group or different groups.

In the General Formula (CDN2-e), preferred examples of the divalent linking group represented by $L_{EP1}$, $L_{EP2}$ and $L_{EP3}$ include those listed as the divalent linking group represented by $L_{EP}$ in the General Formula (CDN1-e).

The polymer obtained by polymerizing a compound represented by the General Formula (CDN1) may be, for example, a polymer obtained by three-dimensionally cross-linking and polymerizing at least three compounds represented by the General Formula (CDN1) with or without a linking group. Examples of the polymer obtained by three-dimensionally crosslinking and polymerizing the compound represented by the General Formula (CDN1) include a compound represented by the following structural formula.

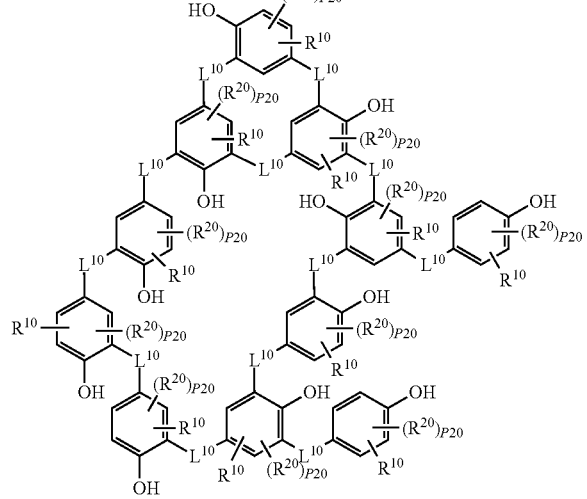

In the above structural formula, $R^{10}$, $R^{20}$ and P20 each independently have the same meanings as $R^1$, $R^2$ and P2 in the General Formula (CDN1). $L^{10}$ represents a single bond or a divalent linking group. A plurality of $R^{10}$ may be the same group or different groups, a plurality of $R^{20}$ may be the same group or different groups, and a plurality of $L^{10}$ may be the same group or different groups. A plurality of P20 may be the same number or different numbers.

In the above structural formula, examples of the divalent linking group represented by $L^{10}$ include an alkylene group optionally having a substituent (preferably an alkylene group having 2 to 30 carbon atoms, and more preferably an alkylene group having 5 to 20 carbon atoms), or the like.

Examples of the substituent contained in the alkylene group include those listed as the substituent for le of the General Formula (CDN1).

The compound represented by the above structural formula may be further modified. For example, the compound may be epoxidized. Specifically, the compound may be a compound having a structure in which the hydroxy group of the compound represented by the above structural formula is replaced by the group (EP), for example, a polymer represented by the following structural formula, i.e., a polymer obtained by three-dimensionally crosslinking and polymerizing the compound represented by the General Formula (CDN1-e).

optionally having a substituent (preferably an alkylene group having 2 to 30 carbon atoms, and more preferably an alkylene group having 5 to 20 carbon atoms), or the like.

Examples of the substituent contained in the alkylene group include those listed as the substituent for le of the General Formula (CDN1).

The cardanol compound (B) preferably contains a cardanol compound having an epoxy group, and is more preferably a cardanol compound having an epoxy group, from the viewpoint of improving a transparency of the resin molded article.

A commercially available product may be used as the cardanol compound (B). Examples of the commercially available product include: NX-2024, Ultra LITE 2023, NX-2026, GX-2503, NC-510, LITE 2020, NX-9001, NX-9004, NX-9007, NX-9008, NX-9201, and NX-9203, manufactured by Cardolite Corporation; LB-7000, LB-7250, and CD-5L manufactured by Tohoku Chemical Industry Co., Ltd.; or the like. Examples of the commercially available product of the cardanol compound having an epoxy group include NC-513, NC-514S, NC-547, LITE 513E, and Ultra LTE 513 manufactured by Cardolite Corporation.

The cardanol compound (B) preferably has a hydroxyl value of 100 mgKOH/g or more, more preferably 120 mgKOH/g or more, and still more preferably 150 mgKOH/g

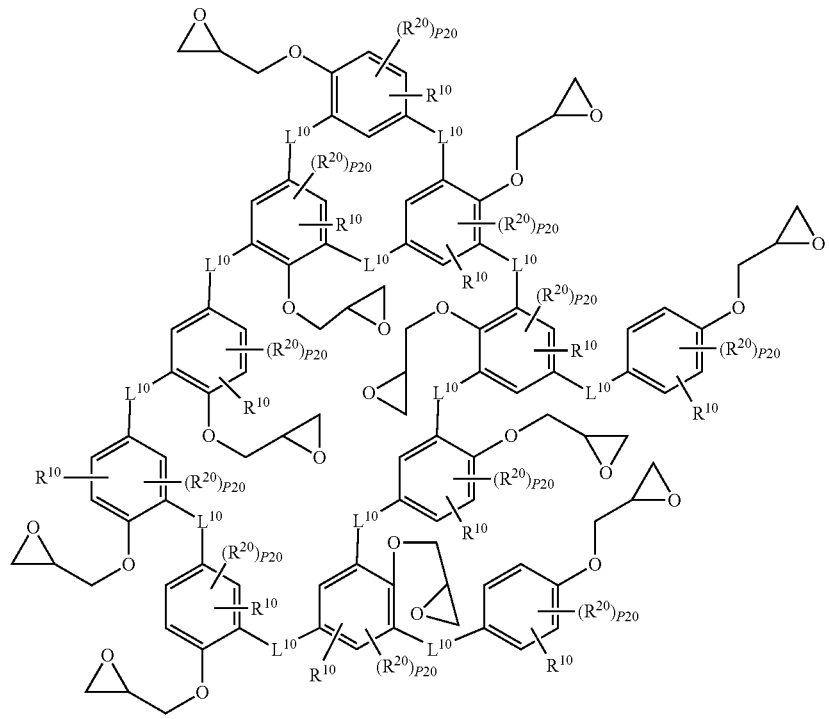

or more, from the viewpoint of obtaining the impact resistance of the resin molded article. The hydroxyl value of the cardanol compound is measured according to a Method A of ISO14900.

When a cardanol compound having an epoxy group is used as the cardanol compound (B), an epoxy equivalent is preferably 300 to 500, more preferably 350 to 480, and still more preferably 400 to 470, from the viewpoint of improving the transparency of the resin molded article. The epoxy In the above structural formula, $R^{10}$, $R^{20}$ and P20 each independently have the same meanings as $R^1$, $R^2$ and P2 in the General Formula (CDN1-e). $L^{10}$ represents a single bond or a divalent linking group. A plurality of $R^{10}$ may be the same group or different groups, a plurality of $R^{20}$ may be the same group or different groups, and a plurality of $L^{10}$ may be the same group or different groups. A plurality of P20 may be the same number or different numbers.

In the above structural formula, examples of the divalent linking group represented by $L^{10}$ include an alkylene group equivalent of the cardanol compound having an epoxy group is measured according to ISO3001.

The cardanol compound (B) preferably has a molecular weight of 250 to 1000, more preferably 280 to 800, and still more preferably 300 to 500, from the viewpoint of easily obtaining the effect of improving the toughness by adding the component (C).

The cardanol compound (B) may be used alone, or may be used in combination of two or more thereof.

[Compound (C): Component (C)]

The compound (C) is at least one selected from the group consisting of a hindered phenol compound, a tocopherol compound, a tocotrienol compound, a phosphite compound, and a hydroxylamine compound.

—Hindered Phenol Compound—

The hindered phenol compound in the present disclosure refers to a compound in which at least one of ortho positions relative to a hydroxy group of a phenol is substituted with an alkyl group. The alkyl group is preferably a bulky alkyl group such as a tert-butyl group, tert-pentyl(1,1-dimethylpropyl) or the like.

Examples of the hindered phenol compound include a compound represented by the following General Formula (HP1).

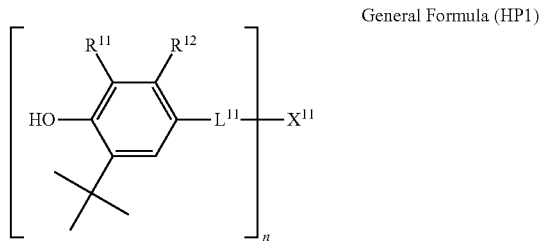

General Formula (HP1)

In the General Formula (HP1), $R^{11}$ and $R^{12}$ each independently represent a hydrogen atom or an alkyl group having 1 to 6 carbon atoms, $L^{11}$ represents a single bond or a divalent linking group, $X^{11}$ represents a single bond or an n-valent group, and n represents 1, 2, 3 or 4.

The alkyl group having 1 to 6 carbon atoms represented by $R^{11}$ is preferably an alkyl group having 1 to 5 carbon atoms, and more preferably an alkyl group having 1 to 4 carbon atoms. The alkyl group having 1 to 6 carbon atoms represented by $R^{11}$ may be linear, branched or cyclic, and is preferably a linear or branched alkyl group.

The alkyl group having 1 to 6 carbon atoms represented by $R^{11}$ is specifically and preferably a methyl group, an ethyl group, an n-propyl group, an isopropyl group, an n-butyl group, a sec-butyl group, an isobutyl group, a tert-butyl group, an n-pentyl group, an isopentyl group, a neopentyl group, a tert-pentyl group, an n-hexyl group, and a 1,1-dimethylbutyl group, more preferably a methyl group, a tert-butyl group or a tert-pentyl group, and still more preferably a methyl group or a tert-butyl group.

The alkyl group having 1 to 6 carbon atoms represented by $R^{11}$ is preferably an alkyl group having 1 to 3 carbon atoms, and more preferably an alkyl group having 1 or 2 carbon atoms. The alkyl group having 1 to 6 carbon atoms represented by $R^{12}$ may be linear, branched or cyclic, and is preferably a linear or branched alkyl group.

The alkyl group having 1 to 6 carbon atoms represented by $R^{12}$ is specifically and preferably a methyl group, an ethyl group, an n-propyl group, an isopropyl group, an n-butyl group, a sec-butyl group, an isobutyl group, a tert-butyl group, an n-pentyl group, an isopentyl group, a neopentyl group, a tert-pentyl group, an n-hexyl group, and a 1,1-dimethylbutyl group, more preferably a methyl group, an ethyl group, an n-propyl group or an isopropyl group, and still more preferably a methyl group or an ethyl group.

The group represented by $R^{11}$ is preferably a hydrogen atom, a methyl group, a tert-butyl group or a tert-pentyl group.

The group represented by $R^{12}$ is preferably a hydrogen atom, a methyl group or an ethyl group.

$R^{11}$ and $R^{12}$ may be bonded to each other to form a ring.

Examples of the divalent linking group represented by $L^{11}$ include an alkylene group having 1 to 6 carbon atoms (preferably, an alkylene group having 1 to 4 carbon atoms), —R—C(=O)O—R'—, or the like. Here, R and R' each independently represent an alkylene group having 1 to 6 carbon atoms (preferably, an alkylene group having 1 to 4 carbon atoms, and more preferably an alkylene group having 1 or 2 carbon atoms) or a phenylene group. —R—C(=O)O—R'— is preferably —CH$_2$CH$_2$—C(=O)O—CH$_2$—.

Examples of a monovalent group represented by $X^{11}$ include an aliphatic hydrocarbon group.

The aliphatic hydrocarbon group may be linear, branched, or may contain an alicyclic ring. The aliphatic hydrocarbon group is preferably an aliphatic hydrocarbon group not containing an alicyclic ring (i.e., a chain aliphatic hydrocarbon group), and more preferably a linear aliphatic hydrocarbon group, from the viewpoint of easily dispersing the compound represented by the General Formula (HP1) in the cellulose acylate (A).

The aliphatic hydrocarbon group may be a saturated aliphatic hydrocarbon group or an unsaturated aliphatic hydrocarbon group. The aliphatic hydrocarbon group is preferably a saturated aliphatic hydrocarbon group, from the viewpoint of easily dispersing the compound represented by the General Formula (HP1) in the cellulose acylate (A).

The aliphatic hydrocarbon group preferably has 1 to 24 carbon atoms, more preferably 6 to 20 carbon atoms, and still more preferably 12 to 18 carbon atoms, from the viewpoint of easily dispersing the compound represented by the General Formula (HP1) in the cellulose acylate (A).

Specific examples of the aliphatic hydrocarbon group include the same groups as those described for $Y^{41}$ in the General Formula (P1) to be described later.

The aliphatic hydrocarbon group is preferably a linear alkyl group having 6 to 20 carbon atoms, more preferably a linear alkyl group having 12 to 18 carbon atoms, and still more preferably a linear alkyl group having 16 to 18 carbon atoms.

Examples of a divalent group represented by $X^{11}$ include a group (an alkanediyl group) obtained by removing two hydrogen atoms from an alkane having 1 to 6 carbon atoms (preferably, an alkane having 1 to 4 carbon atoms), —(R—O—R')$_m$—, or the like. Here, R and R' each independently represent an alkylene group having 1 to 4 carbon atoms or a phenylene group, and m represents 1, 2, 3 or 4 (preferably 1 or 2). —(R—O—R')$_m$— is preferably —(CH$_2$—O—CH$_2$)$_m$—, and more preferably —CH$_2$—O—CH$_2$— and —(CH$_2$—O—CH$_2$)$_2$—.

Examples of the divalent group represented by $X^{11}$ also include the following group (HP1-a). * represents a binding position with $L^{11}$.

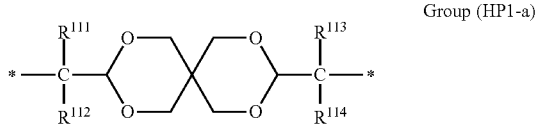

Group (HP1-a)

In the group (HP1-a), $R^{111}$, $R^{112}$, $R^{113}$, and $R^{114}$ each independently represent a hydrogen atom or an alkyl group having 1 to 4 carbon atoms. The alkyl group having 1 to 4 carbon atoms is preferably a methyl group, an ethyl group, an n-propyl group, an isopropyl group, an n-butyl group, a sec-butyl group, an isobutyl group, and a tert-butyl group, more preferably a methyl group or an ethyl group, and still more preferably a methyl group.

Examples of a trivalent group represented by $X^{11}$ include a group (an alkanetriyl group) obtained by removing three hydrogen atoms from an alkane having 1 to 6 carbon atoms (preferably, an alkane having 1 to 4 carbon atoms), or the like.

Examples of the trivalent group represented by $X^{11}$ also include the following groups (HP1-b) and (HP1-c). * represents a binding position with $L^{11}$.

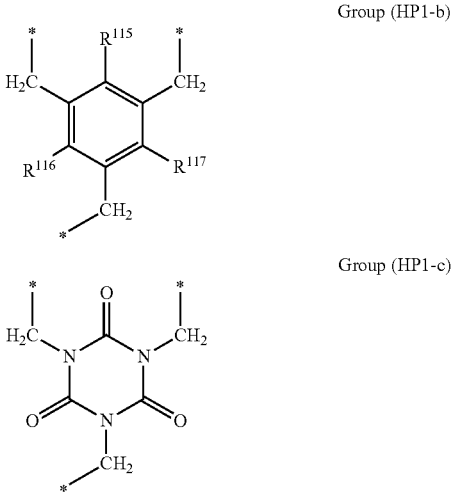

Group (HP1-b)

Group (HP1-c)

In the group (HP1-b), $R^{115}$, $R^{116}$, and $R^{117}$ each independently represent a hydrogen atom or an alkyl group having 1 to 4 carbon atoms. The alkyl group having 1 to 4 carbon atoms is preferably a methyl group, an ethyl group, an n-propyl group, an isopropyl group, an n-butyl group, a sec-butyl group, an isobutyl group, and a tert-butyl group, more preferably a methyl group or an ethyl group, and still more preferably a methyl group.

Examples of a tetravalent group represented by $X^{11}$ include a group (an alkane tetrayl group) obtained by removing four hydrogen atoms from an alkane having 1 to 6 carbon atoms (preferably, an alkane having 1 to 4 carbon atoms), or the like. Of these, a methanetetrayl group is preferred.

A plurality of $R^{11}$ existing when n is 2, 3 or 4 may be the same group or different groups, a plurality of $R^{12}$ existing when n is 2, 3 or 4 may be the same group or different groups, and a plurality of $L^{11}$ existing when n is 2, 3 or 4 may be the same group or different groups.

Specific examples of the compound represented by the General Formula (HP1) include "Irganox 1010", "Irganox 245", and "Irganox 1076" manufactured by BASF; "ADK STAB AO-80", "ADK STAB AO-60", "ADK STAB AO-50", "ADK STAB AO-40", "ADK STAB AO-30", "ADK STAB AO-20", and "ADK STAB AO-330" manufactured by ADEKA Corporation; and "Sumilizer GA-80" manufactured by Sumitomo chemical Co., Ltd.

Examples of the hindered phenol compound include a compound represented by the following General Formula (HP2).

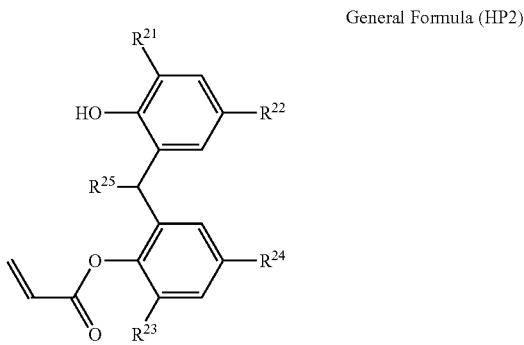

General Formula (HP2)

In the General Formula (HP2), $R^{21}$, $R^{22}$, $R^{23}$, $R^{24}$, and $R^{25}$ each independently represent a hydrogen atom or an alkyl group having 1 to 6 carbon atoms.

The alkyl group having 1 to 6 carbon atoms represented by $R^{21}$ is preferably an alkyl group having 4 to 6 carbon atoms, and more preferably an alkyl group having 4 or 5 carbon atoms. The alkyl group having 1 to 6 carbon atoms represented by $R^{21}$ may be linear, branched or cyclic, and is preferably a linear or branched alkyl group, and more preferably a branched alkyl group.

The alkyl group having 1 to 6 carbon atoms represented by $R^{21}$ is specifically and preferably a methyl group, an ethyl group, an n-propyl group, an isopropyl group, an n-butyl group, a sec-butyl group, an isobutyl group, a tert-butyl group, an n-pentyl group, an isopentyl group, a neopentyl group, a tert-pentyl group, an n-hexyl group, and a 1,1-dimethylbutyl group, more preferably a tert-butyl group, a tert-pentyl group or a 1,1-dimethylbutyl group, and still more preferably a tert-butyl group or a tert-pentyl group.

The alkyl group having 1 to 6 carbon atoms represented by $R^{22}$ is preferably an alkyl group having 1 to 5 carbon atoms, and more preferably an alkyl group having 1 to 4 carbon atoms. The alkyl group having 1 to 6 carbon atoms represented by $R^{22}$ may be linear, branched or cyclic, and is preferably a linear or branched alkyl group.

The alkyl group having 1 to 6 carbon atoms represented by $R^{22}$ is specifically and preferably a methyl group, an ethyl group, an n-propyl group, an isopropyl group, an n-butyl group, a sec-butyl group, an isobutyl group, a tert-butyl group, an n-pentyl group, an isopentyl group, a neopentyl group, a tert-pentyl group, an n-hexyl group, and a 1,1-dimethylbutyl group, and more preferably a methyl group, a tert-butyl group or a tert-pentyl group.

The specific form and preferred form of the group represented by $R^{23}$ are the same as those described for $R^{21}$.

The specific form and preferred form of the group represented by $R^{24}$ are the same as those described for $R^{22}$.

The alkyl group having 1 to 6 carbon atoms represented by $R^{25}$ is preferably an alkyl group having 1 to 3 carbon atoms, and more preferably an alkyl group having 1 or 2 carbon atoms. The alkyl group having 1 to 6 carbon atoms represented by $R^{25}$ may be linear, branched or cyclic, and is preferably a linear or branched alkyl group.

The alkyl group having 1 to 6 carbon atoms represented by $R^{25}$ is specifically and preferably a methyl group, an ethyl group, an n-propyl group, an isopropyl group, an n-butyl group, a sec-butyl group, an isobutyl group, a tert-butyl group, an n-pentyl group, an isopentyl group, a neopentyl group, a tert-pentyl group, an n-hexyl group, and a 1,1-dimethylbutyl group, more preferably a methyl group, an ethyl group, an n-propyl group or an isopropyl group, and still more preferably a methyl group or an ethyl group.

The group represented by $R^{21}$ is preferably a tert-butyl group or a tert-pentyl group.

The group represented by $R^{22}$ is preferably a methyl group, a tert-butyl group or a tert-pentyl group.

The group represented by $R^{23}$ is preferably a tert-butyl group or a tert-pentyl group.

The group represented by $R^{24}$ is preferably a methyl group, a tert-butyl group or a tert-pentyl group.

The group represented by $R^{25}$ is preferably a hydrogen atom, a methyl group or an ethyl group.

Specific examples of the compound represented by the General Formula (HP2) include "Sumilizer GM" and "Sumilizer GS" manufactured by Sumitomo chemical Co., Ltd.

—Tocopherol Compound and Tocotrienol Compound—

Examples of the tocopherol compound or the tocotrienol compound include a compound represented by the following General Formula (T1).

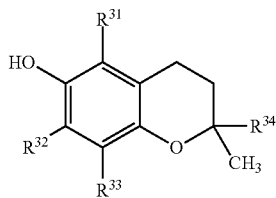

General Formula (T1)

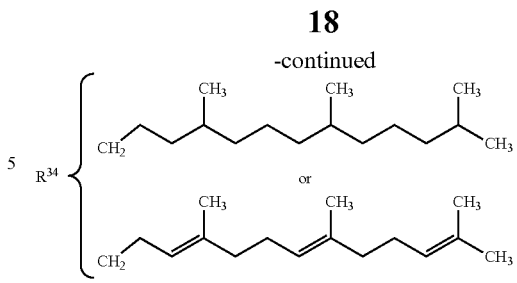

In the General Formula (T1), $R^{31}$, $R^{32}$, and $R^{33}$ each independently represent a hydrogen atom or an alkyl group having 1 to 3 carbon atoms.

The alkyl group having 1 to 3 carbon atoms represented by $R^{31}$ may be linear, branched or cyclic, and is preferably a linear or branched alkyl group.

The alkyl group having 1 to 3 carbon atoms represented by $R^{31}$ is specifically and preferably a methyl group, an ethyl group, an n-propyl group, and an isopropyl group, more preferably a methyl group or an ethyl group, and still more preferably a methyl group.

The group represented by $R^{31}$ is particularly preferably a hydrogen atom, or a methyl group.

The specific form and preferred form of the group represented by $R^{32}$ are the same as those described for $R^{31}$.

The specific form and preferred form of the group represented by $R^{33}$ are the same as those described for $R^{31}$.

Specific examples of the tocopherol compound include the following compounds.

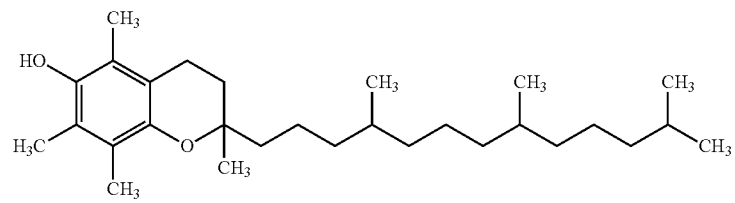

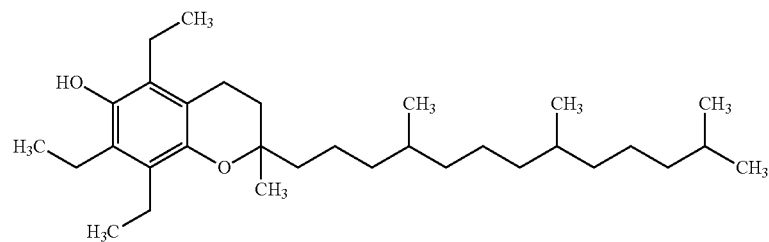

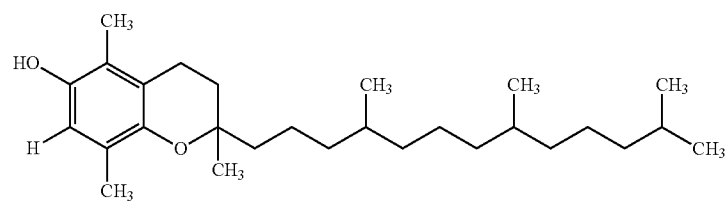

-continued
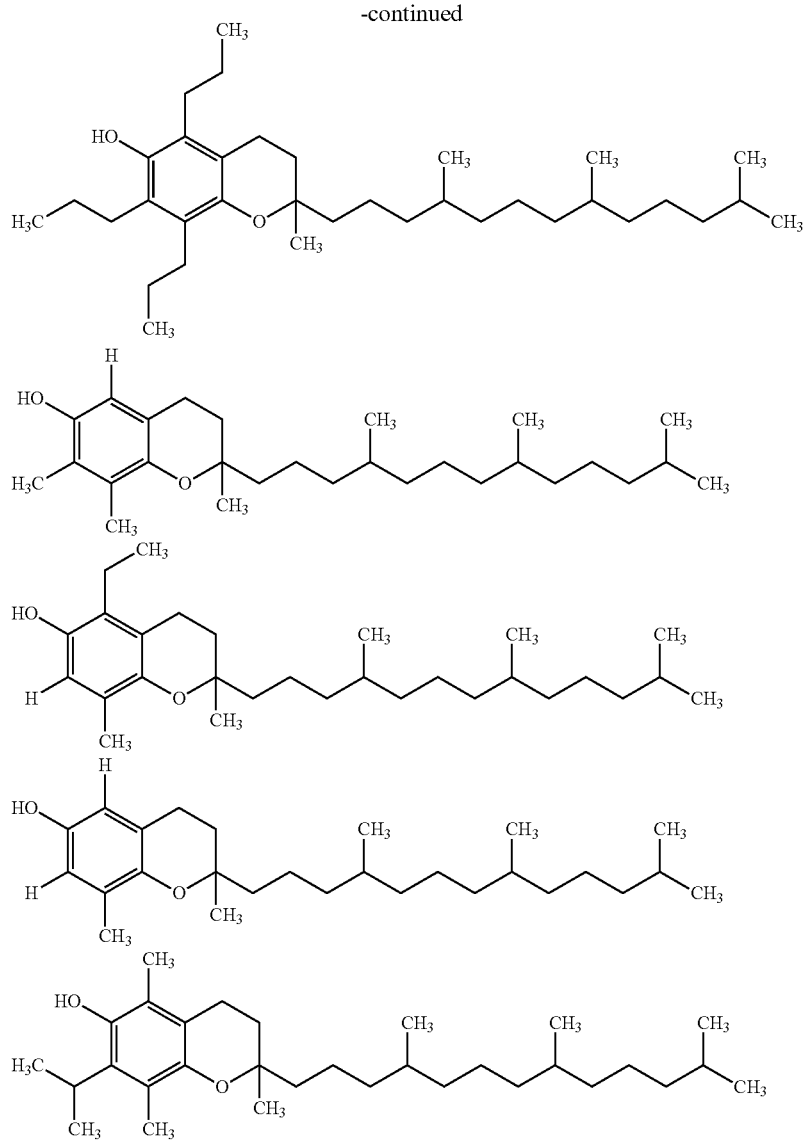
Specific examples of the tocotrienol compound include the following compounds.
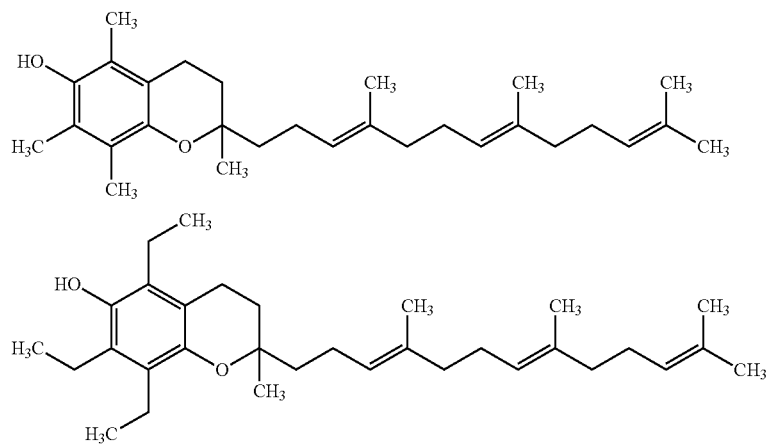

-continued
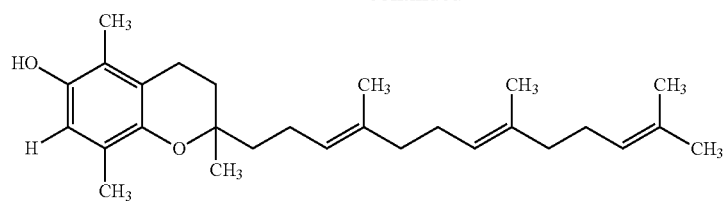
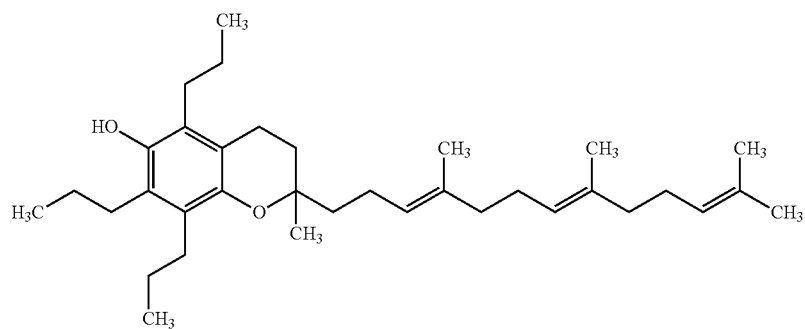
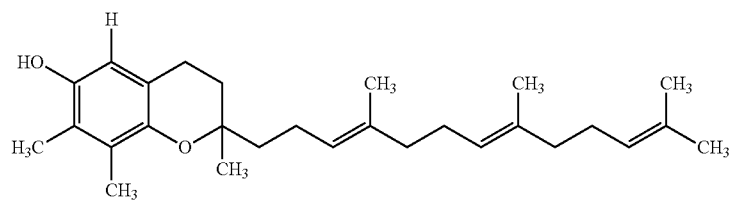
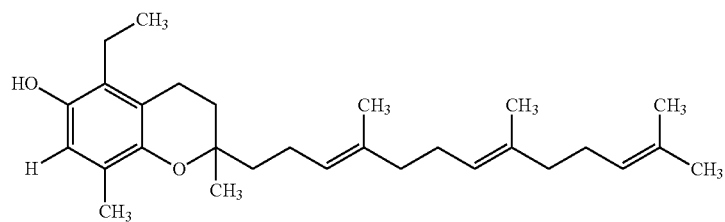
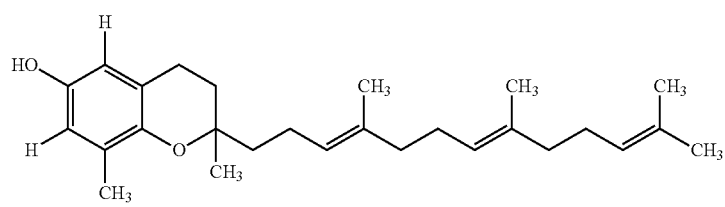
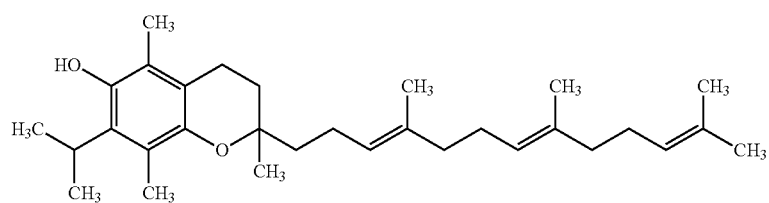

—Phosphite Compound—

Examples of the phosphite compound include a compound represented by the following General Formula (P1).

General Formula (P1)

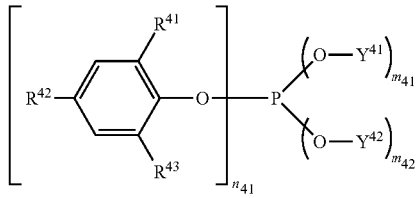

In the General Formula (P1), $R^{41}$, $R^{42}$ and $R^{43}$ each independently represent a hydrogen atom or an alkyl group having 1 to 12 carbon atoms, $Y^{41}$ and $Y^{42}$ each independently represent an aliphatic hydrocarbon group, $n_{41}$ represents 1, 2 or 3, $m_{41}$ represents 0 or 1, $m_{42}$ represents 0 or 1, and $n_{41}+m_{41}+m_{42}=3$.

The alkyl group having 1 to 12 carbon atoms represented by $R^{41}$ is preferably an alkyl group having 1 to 10 carbon atoms, and more preferably an alkyl group having 1 to 9 carbon atoms. The alkyl group having 1 to 12 carbon atoms represented by $R^{41}$ may be linear, branched or cyclic, and is preferably a linear or branched alkyl group.

Specific examples of the alkyl group having 1 to 12 carbon atoms represented by $R^{41}$ include a methyl group, an ethyl group, an n-propyl group, an isopropyl group, an n-butyl group, a sec-butyl group, an isobutyl group, a tert-butyl group, an n-pentyl group, an isopentyl group, a neopentyl group, a tert-pentyl group, an n-hexyl group, an isohexyl group, a sec-hexyl group, a tert-hexyl group, a heptyl group, an isoheptyl group, a sec-heptyl group, a tert-heptyl group, an n-octyl group, an isooctyl group, a sec-octyl group, a tert-octyl group, an n-nonyl group, an isononyl group, a sec-nonyl group, a tert-nonyl group, an n-decyl group, an isodecyl group, a sec-decyl group, a tert-decyl group, an n-undecyl group, an isoundecyl group, a sec-dodecyl group, a tert-dodecyl group, an n-dodecyl group, an isododecyl group, a sec-dodecyl group, and a tert-dodecyl group.

Examples of the alkyl group having 1 to 12 carbon atoms represented by $R^{42}$ include the same forms as those described for $R^{41}$.

Examples of the alkyl group having 1 to 12 carbon atoms represented by $R^{43}$ include the same forms as those described for $R^{41}$.

The group represented by $R^{41}$ is preferably a hydrogen atom, a methyl group or a tert-butyl group.

The group represented by $R^{42}$ is preferably an alkyl group having 1 to 9 carbon atoms, more preferably a methyl group or a tert-butyl group, and still more preferably a tert-butyl group.

The group represented by $R^{43}$ is preferably a hydrogen atom, a methyl group or a tert-butyl group.

A plurality of $R^{41}$ existing when $n_{41}$ is 2 or 3 may be the same group or different groups, a plurality of $R^{42}$ existing when $n_{41}$ is 2 or 3 may be the same group or different groups, and a plurality of $R^{43}$ existing when $n_{41}$ is 2 or 3 may be the same group or different groups.

A plurality of $R^{41}$ existing when $n_{41}$ is 2 or 3 may be linked to each other to form a ring, a plurality of $R^{43}$ existing when $n_{41}$ is 2 or 3 may be linked to each other to form a ring, or $R^{41}$ and $R^{43}$ existing when $n_{41}$ is 2 or 3 may be linked to each other to form a ring.

The aliphatic hydrocarbon group represented by $Y^{41}$ may be linear, branched, or may contain an alicyclic ring. The aliphatic hydrocarbon group represented by $Y^{41}$ is preferably an aliphatic hydrocarbon group not containing an alicyclic ring (i.e., a chain aliphatic hydrocarbon group), and more preferably a linear aliphatic hydrocarbon group, from the viewpoint of easily dispersing the compound represented by the General Formula (P1) in the cellulose acylate (A).

The aliphatic hydrocarbon group represented by $Y^{41}$ may be a saturated aliphatic hydrocarbon group or an unsaturated aliphatic hydrocarbon group. The aliphatic hydrocarbon group represented by $Y^{41}$ is preferably a saturated aliphatic hydrocarbon group, from the viewpoint of easily dispersing the compound represented by the General Formula (P1) in the cellulose acylate (A).

The aliphatic hydrocarbon group represented by $Y^{41}$ preferably has 1 to 20 carbon atoms, more preferably 1 to 12 carbon atoms, and still more preferably 2 to 8 carbon atoms, from the viewpoint of easily dispersing the compound represented by the General Formula (P1) in the cellulose acylate (A).

The specific form and preferred form of the aliphatic hydrocarbon group represented by $Y^{42}$ are the same as those described for $Y^{41}$.

Specific examples of the aliphatic hydrocarbon group represented by $Y^{41}$ and $Y^{42}$ are shown below.

| $Y^{41}, Y^{42}$ | | |
|---|---|---|
| Linear and saturated | Linear and unsaturated | |
| —$CH_3$ | —CH=CH—$CH_3$ | —$CH_2$—CH=CH—$CH_2CH_3$ |
| —$CH_2CH_3$ | —CH=CH—$C_5H_{10}CH_3$ | —$CH_2$—CH=CH—$C_4H_8CH_3$ |
| —$C_3H_6CH_3$ | —CH=CH—$C_9H_{18}CH_3$ | —$CH_2$—CH=CH—$C_8H_{16}CH_3$ |
| —$C_4H_8CH_3$ | —CH=CH—$C_{13}H_{26}CH_3$ | —$CH_2$—CH=CH—$C_{16}H_{32}CH_3$ |
| —$C_5H_{10}CH_3$ | —CH=CH—$C_{17}H_{34}CH_3$ | —$C_3H_6$—CH=CH—$C_7H_{14}CH_3$ |
| —$C_7H_{14}CH_3$ | —$CH_2$—CH=$CH_2$ | —$C_3H_6$—CH=CH—$C_{14}H_{28}CH_3$ |
| —$C_9H_{18}CH_3$ | —$C_6H_{12}$—CH=$CH_2$ | —$C_2H_4$—CH=CH—$C_2H_4CH_3$ |
| —$C_{11}H_{22}CH_3$ | —$C_{10}H_{20}$—CH=$CH_2$ | —$C_4H_8$—CH=CH—$C_4H_8CH_3$ |
| —$C_{13}H_{26}CH_3$ | —$C_{14}H_{28}$—CH=$CH_2$ | —$C_6H_{12}$—CH=CH—$C_6H_{12}CH_3$ |
| —$C_{15}H_{30}CH_3$ | —$C_{18}H_{36}$—CH=$CH_2$ | —$C_8H_{16}$—CH=CH—$C_8H_{16}CH_3$ |
| —$C_{17}H_{34}CH_3$ | —$CH_2$—CH=CH—$C_3H_6$—CH=CH—$C_3H_6CH_3$ | |
| —$C_{19}H_{38}CH_3$ | —$CH_2$—CH=CH—$C_7H_{14}$—CH=CH—$C_7H_{14}CH_3$ | |

| $Y^{41}, Y^{42}$ | |
|---|---|
| Branched and saturated | Branched and unsaturated |
| —$CH(CH_3)_2$ | —CH=CH—$CH(CH_3)_2$ |
| —$C_4H_8$—$CH(CH_3)_2$ | —CH=CH—$C_3H_6$—$CH(CH_3)_2$ |
| —$C_9H_{18}$—$CH(CH_3)_2$ | —CH=CH—$C_9H_{18}$—$CH(CH_3)_2$ |
| —$C_{14}H_{28}$—$CH(CH_3)_2$ | —CH=CH—$C_{15}H_{30}$—$CH(CH_3)_2$ |
| —$C_{17}H_{28}$—$CH(CH_3)_2$ | —CH=CH—$C(CH_3)_3$ |
| —$C(CH_3)_3$ | —CH=CH—$C_3H_6$—$C(CH_3)_3$ |
| —$C_6H_{12}$—$C(CH_3)_3$ | —CH=CH—$C_8H_{16}$—$C(CH_3)_3$ |

-continued

| $Y^{41}, Y^{42}$ | |
|---|---|
| Branched and saturated | Branched and unsaturated |
| —$C_{11}H_{22}$—$C(CH_3)_3$ | —CH=CH—$C_{14}H_{28}$—$C(CH_3)_3$ |
| —$C_{16}H_{32}$—$C(CH_3)_3$ | —CH=CH—$CH(C_2H_5)_2$ |
| —$CH_2$—$CH(C_2H_5)_2$ | —CH=CH—$CH(C_6H_{13})_2$ |
| —$CH_2$—$CH(C_6H_{13})_2$ | —CH=CH—$CH(C_8H_{17})_2$ |
| —$CH_2$—$CH(C_9H_{18})_2$ | —$C_2H_4$—CH=CH—$C_3H_6$—$CH(CH_3)_2$ |
| —$CH(CH_3)$—$C_5H_{10}CH_3$ | —$C_3H_6$—CH=CH—$C_5H_{10}$—$CH(CH_3)_2$ |
| —$CH(CH_3)$—$C_{12}H_{24}CH_3$ | —$C_7H_{14}$—CH=CH—$C_7H_{14}$—$CH(CH_3)_2$ |
| —$CH(CH_3)$—$C_{16}H_{32}CH_3$ | —$CH(CH_3)$—$C_5H_{10}$—CH=$CH_2$ |
| —$CH(C_2H_5)$—$C_3H_6CH_3$ | —$CH(CH_3)$—$C_{16}H_{32}$—CH=$CH_2$ |
| —$CH(C_2H_5)$—$C_{16}H_{32}CH_3$ | —$C_4H_8$—CH=CH—$C_4H_8$—CH=CH—$C_4H_8$—$CH(CH_3)_2$ |

$n_{41}$ represents 1, 2 or 3, preferably 2 or 3, and more preferably 3.

In the General Formula (P1), specific examples of the compound when $n_{41}=2$ include "Irgafos 38" (bis(2,4-di-t-butyl-6-methylphenyl)-ethyl-phosphite) manufactured by BASF.

In the General Formula (P1), the compound represented by the General Formula (P1) when $n_{41}=3$ include a compound represented by the following General Formula (P1-a).

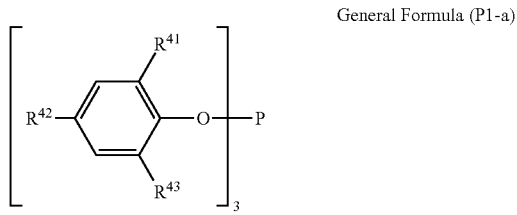

General Formula (P1-a)

$R^{41}$, $R^{42}$ and $R^{43}$ in the General Formula (P1-a) have the same meaning as $R^{41}$, $R^{42}$ and $R^{43}$ in the General Formula (P1).

Specific examples of the compound represented by the General Formula (P1-a) include "Irgafos 168" and "Irgafos TNPP" manufactured by BASF.

Examples of the phosphite compound include a compound represented by the following General Formula (P2).

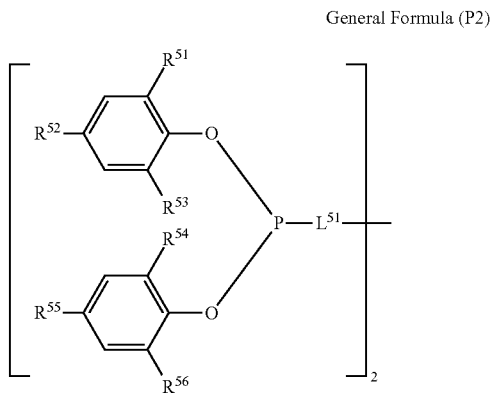

General Formula (P2)

In the General Formula (P2), $R^{51}$, $R^{52}$, $R^{53}$, $R^{54}$, $R^{55}$, and $R^{56}$ each independently represent a hydrogen atom or an alkyl group having 1 to 12 carbon atoms, and $L^{51}$ represents a single bond or a divalent linking group.

The alkyl group having 1 to 12 carbon atoms represented by $R^{51}$ is preferably an alkyl group having 1 to 10 carbon atoms, and more preferably an alkyl group having 1 to 9 carbon atoms. The alkyl group having 1 to 12 carbon atoms represented by $R^{51}$ may be linear, branched or cyclic, and is preferably a linear or branched alkyl group.

Specific examples of the alkyl group having 1 to 12 carbon atoms represented by $R^{51}$ include a methyl group, an ethyl group, an n-propyl group, an isopropyl group, an n-butyl group, a sec-butyl group, an isobutyl group, a tert-butyl group, an n-pentyl group, an isopentyl group, a neopentyl group, a tert-pentyl group, an n-hexyl group, an isohexyl group, a sec-hexyl group, a tert-hexyl group, a heptyl group, an isoheptyl group, a sec-heptyl group, a tert-heptyl group, an n-octyl group, an isooctyl group, a sec-octyl group, a tert-octyl group, an n-nonyl group, an isononyl group, a sec-nonyl group, a tert-nonyl group, an n-decyl group, an isodecyl group, a sec-decyl group, a tert-decyl group, an n-undecyl group, an isoundecyl group, a sec-dodecyl group, a tert-dodecyl group, an n-dodecyl group, an isododecyl group, a sec-dodecyl group, and a tert-dodecyl group.

Examples of the alkyl group having 1 to 12 carbon atoms represented by $R^{52}$ include the same forms as those described for $R^{51}$.

Examples of the alkyl group having 1 to 12 carbon atoms represented by $R^{53}$ include the same forms as those described for $R^{51}$.

Examples of the alkyl group having 1 to 12 carbon atoms represented by $R^{54}$ include the same forms as those described for $R^{51}$.

Examples of the alkyl group having 1 to 12 carbon atoms represented by $R^{55}$ include the same forms as those described for $R^{51}$.

Examples of the alkyl group having 1 to 12 carbon atoms represented by $R^{56}$ include the same forms as those described for $R^{51}$.

The group represented by $R^{51}$ is preferably a hydrogen atom, a methyl group or a tert-butyl group.

The group represented by $R^{52}$ is preferably an alkyl group having 1 to 9 carbon atoms, more preferably a methyl group or a tert-butyl group, and still more preferably a tert-butyl group.

The group represented by $R^{53}$ is preferably a hydrogen atom, a methyl group or a tert-butyl group.

The group represented by $R^{54}$ is preferably a hydrogen atom, a methyl group or a tert-butyl group.

The group represented by $R^{55}$ is preferably an alkyl group having 1 to 9 carbon atoms, more preferably a methyl group or a tert-butyl group, and still more preferably a tert-butyl group.

The group represented by $R^{56}$ is preferably a hydrogen atom, a methyl group or a tert-butyl group.

Examples of the divalent linking group represented by $L^{51}$ include an alkylene group or an arylene group, preferably an alkylene group having 1 to 6 carbon atoms or a phenylene group, and more preferably an alkylene group having 1 to 4 carbon atoms or a phenylene group.

Specific examples of the compound represented by the General Formula (P2) include "Irgafos P-EPQ" manufactured by BASF.

Examples of the phosphite compound include a compound represented by the following General Formula (P3).

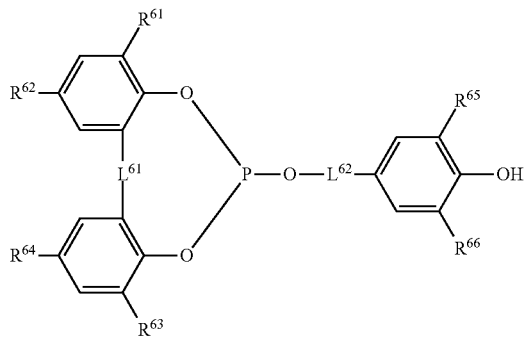

General Formula (P3)

In the General Formula (P3), $R^{61}$, $R^{62}$, $R^{63}$, $R^{64}$, $R^{65}$, and $R^{66}$ each independently represent a hydrogen atom or an alkyl group having 1 to 12 carbon atoms, and $L^{61}$ and $L^{62}$ each independently represent a single bond or a divalent linking group.

The alkyl group having 1 to 12 carbon atoms represented by $R^{61}$ is preferably an alkyl group having 1 to 10 carbon atoms, and more preferably an alkyl group having 1 to 9 carbon atoms. The alkyl group having 1 to 12 carbon atoms represented by $R^{61}$ may be linear, branched or cyclic, and is preferably a linear or branched alkyl group.

Specific examples of the alkyl group having 1 to 12 carbon atoms represented by $R^{61}$ include a methyl group, an ethyl group, an n-propyl group, an isopropyl group, an n-butyl group, a sec-butyl group, an isobutyl group, a tert-butyl group, an n-pentyl group, an isopentyl group, a neopentyl group, a tert-pentyl group, an n-hexyl group, an isohexyl group, a sec-hexyl group, a tert-hexyl group, a heptyl group, an isoheptyl group, a sec-heptyl group, a tert-heptyl group, an n-octyl group, an isooctyl group, a sec-octyl group, a tert-octyl group, an n-nonyl group, an isononyl group, a sec-nonyl group, a tert-nonyl group, an n-decyl group, an isodecyl group, a sec-decyl group, a tert-decyl group, an n-undecyl group, an isoundecyl group, a sec-dodecyl group, a tert-dodecyl group, an n-dodecyl group, an isododecyl group, a sec-dodecyl group, and a tert-dodecyl group.

Examples of the alkyl group having 1 to 12 carbon atoms represented by $R^{62}$ include the same forms as those described for $R^{61}$.

Examples of the alkyl group having 1 to 12 carbon atoms represented by $R^{63}$ include the same forms as those described for $R^{61}$.

Examples of the alkyl group having 1 to 12 carbon atoms represented by $R^{64}$ include the same forms as those described for $R^{61}$.

Examples of the alkyl group having 1 to 12 carbon atoms represented by $R^{65}$ include the same forms as those described for $R^{61}$.

Examples of the alkyl group having 1 to 12 carbon atoms represented by $R^{66}$ include the same forms as those described for $R^{61}$.

The group represented by $R^{61}$ is preferably a hydrogen atom, a methyl group or a tert-butyl group.

The group represented by $R^{62}$ is preferably an alkyl group having 1 to 9 carbon atoms, more preferably a methyl group or a tert-butyl group, and still more preferably a tert-butyl group.

The group represented by $R^{63}$ is preferably a hydrogen atom, a methyl group or a tert-butyl group.

The group represented by $R^{64}$ is preferably an alkyl group having 1 to 9 carbon atoms, more preferably a methyl group or a tert-butyl group, and still more preferably a tert-butyl group.

The group represented by $R^{65}$ is preferably a hydrogen atom, a methyl group, a tert-butyl group or a tert-pentyl group.

The group represented by $R^{66}$ is preferably a hydrogen atom, a methyl group, a tert-butyl group or a tert-pentyl group.

It is preferable that at least one of $R^{65}$ and $R^{66}$ is an alkyl group, and the alkyl group is preferably a tert-butyl group or a tert-pentyl group.

Examples of the divalent linking group represented by $L^{61}$ include an alkylene group, preferably an alkylene group having 1 to 3 carbon atoms, and more preferably an alkylene group having 1 or 2 carbon atoms.

$L^{61}$ is particularly preferably a single bond or a methylene group.

Examples of the divalent linking group represented by $L^{62}$ include an alkylene group and an arylene group, preferably an alkylene group having 1 to 6 carbon atoms or a phenylene group, and more preferably an alkylene group having 1 to 4 carbon atoms or a phenylene group.

Specific examples of the compound represented by the General Formula (P3) include "Sumilizer GP" manufactured by Sumitomo chemical Co., Ltd.

—Hydroxylamine Compound—

The hydroxylamine compound in the present disclosure refers to a compound having a structure in which at least one hydroxy group is directly bonded to a nitrogen atom of an amine. The hydroxylamine compound is preferably N,N-dialkylhydroxylamine.

Examples of the hydroxylamine compound include a compound represented by the following General Formula (HA1).

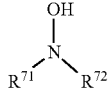

General Formula (HA1)

In the General Formula (HA1), $R^{71}$ and $R^{72}$ each independently represent an alkyl group having 14 to 20 carbon atoms.

The alkyl group having 14 to 20 carbon atoms represented by $R^{71}$ may be any one of a linear alkyl group, a branched alkyl group and an alkyl group containing an alicyclic ring, preferably a linear or branched alkyl group, and more preferably a linear alkyl group.

When the alkyl group having 14 to 20 carbon atoms represented by $R^{71}$ is branched, the number of branched chains in the alkyl group is preferably 1 to 3, more preferably 1 or 2, and still more preferably 1.

The alkyl group having 14 to 20 carbon atoms represented by $R^{71}$ is preferably a linear or branched alkyl group having 16 to 18 carbon atoms, and particularly preferably a linear alkyl group having 16 to 18 carbon atoms.

The specific form and preferred form of the group represented by $R^{72}$ are the same as those described for $R^{71}$.

Specific examples of the alkyl group having 14 to 20 carbon atoms represented by $R^{71}$ and $R^{72}$ are shown below.

| $R^{71}, R^{72}$ | | |
|---|---|---|
| Linear | Branched | |
| —$C_{13}H_{26}CH_3$ | —$C_{11}H_{22}$—$CH(CH_3)_2$ | —$CH(CH_3)$—$C_{11}H_{22}CH_3$ |
| —$C_{14}H_{28}CH_3$ | —$C_{13}H_{26}$—$CH(CH_3)_2$ | —$CH(CH_3)$—$C_{13}H_{26}CH_3$ |
| —$C_{15}H_{30}CH_3$ | —$C_{14}H_{28}$—$CH(CH_3)_2$ | —$CH(CH_3)$—$C_{14}H_{28}CH_3$ |
| —$C_{16}H_{32}CH_3$ | —$C_{15}H_{30}$—$CH(CH_3)_2$ | —$CH(CH_3)$—$C_{15}H_{30}CH_3$ |
| —$C_{17}H_{34}CH_3$ | —$C_{17}H_{34}$—$CH(CH_3)_2$ | —$CH(CH_3)$—$C_{17}H_{34}CH_3$ |
| —$C_{18}H_{36}CH_3$ | —$C_{10}H_{20}$—$C(CH_3)_3$ | —$CH_2$—$CH(CH_3)$—$C_{10}H_{20}CH_3$ |
| —$C_{19}H_{38}CH_3$ | —$C_{12}H_{24}$—$C(CH_3)_3$ | —$CH_2$—$CH(CH_3)$—$C_{12}H_{24}CH_3$ |
| | —$C_{14}H_{28}$—$C(CH_3)_3$ | —$CH_2$—$CH(CH_3)$—$C_{14}H_{28}CH_3$ |
| | —$C_{16}H_{32}$—$C(CH_3)_3$ | —$CH_2$—$CH(CH_3)$—$C_{16}H_{32}CH_3$ |
| | —$C_3H_6$—$CH(CH_3)$—$C_3H_6$—$CH(CH_3)$—$C_5H_{10}CH_3$ | |
| | —$C_3H_6$—$CH(CH_3)$—$C_3H_6$—$CH(CH_3)$—$C_7H_{14}CH_3$ | |

Specific examples of the compound represented by the General Formula (HA1) include "Irgastab FS-042" manufactured by BASF.

The compound (C) may be used alone, or may be used in combination of two or more thereof. The form of using two or more kinds of the compound (C) in combination includes a form using two or more kinds of the compound (C) within the same family in combination (for example, within the hindered phenol compound), or a form using two or more kinds of the compound (C) within different families in combination (for example, the hindered phenol compound and the tocopherol compound).

The form of using two or more kinds of the compound (C) in combination is preferably a form in which at least one selected from the group consisting of a hindered phenol compound and a hydroxylamine compound and at least one selected from phosphite compounds are used in combination.

[Thermoplastic Elastomer (D): Component (D)]

The thermoplastic elastomer (D) is, for example, a thermoplastic elastomer having elasticity at ordinary temperature (25° C.) and softening at a high temperature like a thermoplastic resin.

Examples of the thermoplastic elastomer (D) include:

a core-shell structure polymer (d1), which includes a core layer and a shell layer containing an alkyl (meth)acrylate polymer on a surface of the core layer of the core-shell structure polymer (d1);

an olefin polymer (d2), which is a polymer of an α-olefin and an alkyl (meth)acrylate and contains 60% by mass or more of a structural unit derived from the α-olefin;

a core-shell structure polymer (d3), which includes a core layer containing a butadiene polymer, and a shell layer containing a polymer selected from a styrene polymer and an acrylonitrile-styrene polymer on a surface of the core layer of the core-shell structure polymer (d3);

a styrene-ethylene-butadiene-styrene copolymer (d4);

a polyurethane (d5); and a polyester (d6).

The thermoplastic elastomer (D) is preferably the core-shell structure polymer (d1) or the olefin polymer (d2) from the viewpoint of obtaining excellent Charpy impact strength or toughness of the resin molded article, and more preferably the core-shell structure polymer (d1).

—Core-Shell Structure Polymer (d1): Component (d1)—

The core-shell structure polymer (d1) is a polymer having a core-shell structure with a core layer and a shell layer on a surface of the core layer.

The core-shell structure polymer (d1) is a polymer having a core layer as the innermost layer and a shell layer as the outermost layer (specifically, a polymer having a shell layer obtained by graft-polymerizing an alkyl (meth)acrylate polymer to a core layer polymer).

One or more other layers (for example, one to six other layers) may be provided between the core layer and the shell layer. When another layer is provided between the core layer and the shell layer, the core-shell structure polymer (d1) is a multi-layer polymer obtained by grafting and polymerizing a plurality of polymers to a core layer polymer.

The core layer is not particularly limited, and is preferably a rubber layer. Examples of the rubber layer include a layer of a (meth)acrylic rubber, a silicone rubber, a styrene rubber, a conjugated diene rubber, an α-olefin rubber, a nitrile rubber, a urethane rubber, a polyester rubber, a polyamide rubber, and a copolymer rubber of two or more thereof. Of these, the rubber layer is preferably a layer of a (meth)acrylic rubber, a silicone rubber, a styrene rubber, a conjugated diene rubber, an α-olefin rubber, and a copolymer rubber of two or more thereof. The rubber layer may be crosslinked by copolymerizing crosslinking agents (divinylbenzene, allyl acrylate, butylene glycol diacrylate or the like).

Examples of the (meth)acrylic rubber include a polymer rubber obtained by polymerizing a (meth)acrylic component (for example, alkyl esters of (meth)acrylic acid having 2 to 8 carbon atoms).

Examples of the silicone rubber include a rubber containing a silicone component (polydimethylsiloxane, polyphenylsiloxane, or the like).

Examples of the styrene rubber include a polymer rubber obtained by polymerizing a styrene component (styrene, α-methylstyrene, or the like).

Examples of the conjugated diene rubber include a polymer rubber obtained by polymerizing a conjugated diene component (butadiene, isoprene, or the like).

Examples of the α-olefin rubber include a polymer rubber obtained by polymerizing an α-olefin component (ethylene, propylene, and 2-methylpropylene).

Examples of the copolymer rubber include a copolymer rubber obtained by polymerizing two or more kinds of (meth)acrylic components, a copolymer rubber obtained by polymerizing a (meth)acrylic component and a silicone component, and a copolymer of a (meth)acrylic component, a conjugated diene component and a styrene component, or the like.

Examples of the alkyl (meth)acrylate in the polymer constituting the shell layer include methyl (meth)acrylate, ethyl (meth)acrylate, n-propyl (meth)acrylate, n-butyl (meth)acrylate, t-butyl (meth)acrylate, n-hexyl (meth)acrylate, 2-ethylhexyl (meth)acrylate, cyclohexyl (meth)acrylate, octadecyl (meth)acrylate, or the like. In the alkyl (meth)acrylate, at least a part of the hydrogen of the alkyl chain may be substituted. Examples of the substituent in the alkyl (meth)acrylate include an amino group, a hydroxy group, a halogeno group, or the like.

Of these, the alkyl (meth)acrylate polymer is preferably an alkyl (meth)acrylate polymer having an alkyl chain with 1 to 8 carbon atoms, more preferably an alkyl (meth)acrylate polymer having an alkyl chain with 1 to 2 carbon atoms, and still more preferably an alkyl (meth)acrylate polymer having an alkyl chain with 1 carbon atom, from the viewpoint of obtaining the excellent Charpy impact strength.

The polymer constituting the shell layer may be, in addition to the alkyl (meth)acrylate, a polymer obtained by polymerizing at least one selected from a glycidyl group-containing vinyl compound and an unsaturated dicarboxylic anhydride.

Examples of the glycidyl group-containing vinyl compound include glycidyl (meth)acrylate, glycidyl itaconate, diglycidyl itaconate, allyl glycidyl ether, styrene-4-glycidyl ether, 4-glycidyl styrene, or the like.

Examples of the unsaturated dicarboxylic anhydride include maleic anhydride, itaconic anhydride, glutaconic anhydride, citraconic anhydride, aconitic anhydride, or the like. Of these, maleic anhydride is preferred.

When another layer is provided between the core layer and the shell layer, a layer of a polymer described for the shell layer is exemplified as another layer.

The mass percentage of the shell layer to the entire core-shell structure is preferably from 1% by mass to 40% by mass, more preferably from 3% by mass to 30% by mass, and still more preferably from 5% by mass to 15% by mass.

An average primary particle diameter of the core-shell structure polymer is not particularly limited, and is preferably 50 nm to 500 nm, more preferably 50 nm to 400 nm, still more preferably 100 nm to 300 nm, and particularly preferably 150 nm to 250 nm, from the viewpoint of obtaining the excellent Charpy impact strength.

The average primary particle diameter refers to a value measured by the following method. Particles are observed with a scanning electron microscope, the maximum diameter of the primary particles is taken as a primary particle diameter, and the primary particle diameter of 100 particles is measured and averaged to obtain the average primary particle diameter. Specifically, the average primary particle diameter is obtained by observing a dispersed form of the core-shell structure polymer in the resin composition with a scanning electron microscope.

The core-shell structure polymer (d1) may be prepared by a known method.

Examples of the known method include an emulsion polymerization method. Specifically, the following method is exemplified as a manufacturing method. First, a mixture of monomers is subjected to emulsion polymerization to prepare core particles (core layer), and thereafter a mixture of other monomers is subjected to emulsion polymerization in the presence of the core particles (core layer) to prepare a core-shell structure polymer forming a shell layer around the core particles (core layer). When another layer is formed between the core layer and the shell layer, the emulsion polymerization of the mixture of other monomers is repeated to obtain a desired core-shell structure polymer including the core layer, another layer and the shell layer.

Examples of the commercially available product of the core-shell structure polymer (d1) include "METABLEN" (Registered trademark) manufactured by Mitsubishi Chemical Corporation, "Kane Ace" (Registered trademark) manufactured by Kaneka Corporation, "PARALOID" (Registered trademark) manufactured by the Dow Chemical Japan, "STAPHYLOID" (Registered trademark) manufactured by Aica Kogyo Company, Limited, "Paraface" (Registered trademark) manufactured by KURARAY CO., LTD., or the like.

—Olefin Polymer (d2): Component (d2)—

The olefin polymer (d2) is a polymer of an α-olefin and an alkyl (meth)acrylate and preferably contains 60% by mass or more of a structural unit derived from the α-olefin.

Examples of the α-olefin in the olefin polymer include ethylene, propylene, 2-methylpropylene, or the like. An α-olefin having 2 to 8 carbon atoms is preferred, and an α-olefin having 2 to 3 carbon atoms is more preferred, from the viewpoint of obtaining the excellent Charpy impact strength. Of these, ethylene is still more preferred.

Examples of the alkyl (meth)acrylate polymerizing with the α-olefin include methyl (meth)acrylate, ethyl (meth)acrylate, n-propyl (meth)acrylate, n-butyl (meth)acrylate, t-butyl (meth)acrylate, n-hexyl (meth)acrylate, 2-ethylhexyl (meth)acrylate, cyclohexyl (meth)acrylate, octadecyl (meth)acrylate, or the like. From the viewpoint of obtaining the excellent Charpy impact strength, an alkyl (meth)acrylate having an alkyl chain with 1 to 8 carbon atoms is preferred, an alkyl (meth)acrylate having an alkyl chain with 1 to 4 carbon atoms is more preferred, and an alkyl (meth)acrylate having an alkyl chain with 1 to 2 carbon atoms is still more preferred.

The olefin polymer is preferably a polymer of ethylene and methyl acrylate from the viewpoint of obtaining the excellent Charpy impact strength.

The olefin polymer preferably contains 60% by mass to 97% by mass and more preferably 70% by mass to 85% by mass of a structural unit derived from the α-olefin, from the viewpoint of obtaining the excellent Charpy impact strength.

The olefin polymer may contains other structural units in addition to the structural unit derived from the α-olefin and a structural unit derived from an alkyl (meth)acrylate. However, another structural unit is preferably 10% by mass or less based on all of the structural units in the olefin polymer.

—Core-Shell Structure Polymer (d3): Component (d3)—

The core-shell structure polymer (d3) is a polymer having a core-shell structure with a core layer and a shell layer on a surface of the core layer.

The core-shell structure polymer (d3) is a polymer having a core layer as the innermost layer and a shell layer as the outermost layer (specifically, a polymer having a shell layer obtained by graft-polymerizing a styrene polymer or an acrylonitrile-styrene polymer to a core layer containing a butadiene polymer).

One or more other layers (for example, one to six other layers) may be provided between the core layer and the shell layer. When another layer is provided between the core layer and the shell layer, the core-shell structure polymer (d3) is a multi-layer polymer obtained by grafting and polymerizing a plurality of polymers to a core layer polymer.

The core layer containing a butadiene polymer is not particularly limited as long as it contains a polymer obtained by polymerizing a component containing butadiene, and may be a core layer containing a homopolymer of butadiene, or a core layer containing a copolymer of butadiene and another monomer. When the core layer contains a copolymer of butadiene and another monomer, examples of another monomer include vinyl aromatic monomers. Of the vinyl aromatic monomers, styrene components (for example, styrene, an alkyl-substituted styrene (e.g., α-methyl styrene, 2-methyl styrene, 3-methyl styrene, 4-methyl styrene, 2-ethylstyrene, 3-ethylstyrene, and 4-ethylstyrene), and a halogen-substituted styrene (e.g., 2-chlorostyrene, 3-chlorostyrene, and 4-chlorostyrene)) are preferred. The styrene component may be used alone, or may be used in combination of two or more thereof. Of these styrene components, styrene is preferably used. Polyfunctional monomers such as an allyl (meth)acrylate, a triallyl isocyanurate, and divinylbenzene may be used as another monomer.

Specifically, the core layer containing a butadiene polymer may be, for example, a homopolymer of butadiene, a copolymer of butadiene and styrene, or a terpolymer of butadiene, styrene and divinylbenzene.

The butadiene polymer contained in the core layer contains 60% by mass to 100% by mass (preferably, 70% by mass to 100% by mass) of a structural unit derived from butadiene and 0% by mass to 40% by mass (preferably, 0% by mass to 30% by mass) of a structural unit derived from another monomer (preferably, a styrene component). For example, a percentage of the structural unit derived from each monomer constituting the butadiene polymer is preferably from 60% by mass to 100% by mass for butadiene and from 0% by mass to 40% by mass for styrene. The percentage is preferably from 0% by mass to 5% by mass for divinylbenzene based on the total amount of styrene and divinylbenzene.

The shell layer containing a styrene polymer is not particularly limited as long as it is a shell layer containing a polymer obtained by polymerizing a styrene component, and may be a shell layer containing a homopolymer of styrene, or a shell layer containing a copolymer of styrene and another monomer. Examples of the styrene component include the styrene component as exemplified for the core layer. Examples of another monomer include alkyl (meth)acrylates (for example, methyl (meth)acrylate, ethyl (meth)acrylate, n-propyl (meth)acrylate, n-butyl (meth)acrylate, t-butyl (meth)acrylate, n-hexyl (meth)acrylate, 2-ethylhexyl (meth)acrylate, cyclohexyl (meth)acrylate, and octadecyl (meth)acrylate), or the like. In the alkyl (meth)acrylate, at least a part of the hydrogen of the alkyl chain may be substituted. Examples of the substituent in the alkyl (meth)acrylate include an amino group, a hydroxy group, a halogeno group, or the like. The alkyl (meth)acrylate may be used alone, or may be used in combination of two or more thereof. Polyfunctional monomers such as an allyl (meth)acrylate, a triallyl isocyanurate, and divinylbenzene may be used as another monomer. The styrene polymer contained in the shell layer is preferably a copolymer of a styrene component in an amount of 85% by mass to 100% by mass and another monomer component (preferably, an alkyl (meth)acrylate) in an amount of 0% by mass to 15% by mass.

Of these, the styrene polymer contained in the shell layer is preferably a copolymer of styrene and an alkyl (meth)acrylate from the viewpoint of obtaining the excellent Charpy impact strength. From the same viewpoint, a copolymer of styrene and an alkyl (meth)acrylate having an alkyl chain with 1 to 8 carbon atoms is preferred, and an alkyl (meth)acrylate polymer having an alkyl chain with 1 to 4 carbon atoms is more preferred.

The shell layer containing an acrylonitrile-styrene polymer is a shell layer containing a copolymer of an acrylonitrile component and a styrene component. The acrylonitrile-styrene polymer is not particularly limited and examples thereof include a known acrylonitrile-styrene polymer. Examples of the acrylonitrile-styrene polymer include a copolymer of an acrylonitrile component in an amount of 10% by mass to 80% by mass and a styrene component in an amount of 20% by mass to 90% by mass. Examples of the styrene component copolymerizing with the acrylonitrile component include the styrene component as exemplified for the core layer. Polyfunctional monomers such as an allyl (meth)acrylate, triallyl isocyanurate, divinylbenzene or the like may be used as the acrylonitrile-styrene polymer contained in the shell layer.

When another layer is provided between the core layer and the shell layer, a layer of a polymer described for the shell layer is exemplified as another layer.

The mass percentage of the shell layer to the entire core-shell structure is preferably from 1% by mass to 40% by mass, more preferably from 3% by mass to 30% by mass, and still more preferably from 5% by mass to 15% by mass.

Of the component (d3), examples of the commercially available product of the core-shell structure polymer (d3) including a core layer containing a butadiene polymer and a shell layer containing a styrene polymer on a surface of the core layer include "METABLEN" (registered trademark) manufactured by Mitsubishi Chemical Corporation, "Kane Ace" (Registered trademark) manufactured by Kaneka Corporation, "Clearstrength" (registered trademark) manufactured by Arkema, and "PARALOID" (Registered trademark) manufactured by the Dow Chemical Japan.

Of the component (d3), examples of the commercially available product of the core-shell structure polymer (d3) including a core layer containing a butadiene polymer and a shell layer containing an acrylonitrile-styrene polymer on a surface of the core layer include "Blendex" (registered trademark) manufactured by Galata Chemicals, "ELIX" manufactured by ELIX POLYMERS, or the like.

—Styrene-Ethylene-Butadiene-Styrene Copolymer (d4): Component (d4)—

The copolymer (d4) is not particularly limited as long as it is a thermoplastic elastomer, and examples thereof include a known styrene-ethylene-butadiene-styrene copolymer. The copolymer (d4) may be a styrene-ethylene-butadiene-styrene copolymer and a hydrogenated product thereof.

The copolymer (d4) is preferably a hydrogenated product of the styrene-ethylene-butadiene-styrene copolymer from the viewpoint of obtaining the excellent Charpy impact strength. From the same viewpoint, the copolymer (d4) is preferably a block copolymer, and, for example, is preferably a copolymer (styrene-ethylene/butylene-styrene triblock copolymer) having a block of a styrene portion at both ends and a block of a central portion containing ethylene/butylene by hydrogenating at least a part of a double bond of a butadiene portion. The ethylene/butylene block portion of the styrene-ethylene/butylene-styrene copolymer may be a random copolymer.

The copolymer (d4) is obtained by a known method. When the copolymer (d4) is a hydrogenated product of the styrene-ethylene-butadiene-styrene copolymer, for example, the copolymer (d4) may be obtained by hydrogenating a butadiene portion of a styrene-butadiene-styrene block copolymer in which a conjugated diene portion includes a 1,4 bond.

Examples of the commercially available product of the copolymer (d4) include "Kraton" (registered trademark) manufactured by Kraton Corporation, "Septon" (registered trademark) manufactured by Kuraray CO., LTD., or the like.

—Polyurethane (d5): Component (d5)—

The polyurethane (d5) is not particularly limited as long as it is a thermoplastic elastomer, and examples thereof include a known polyurethane. The polyurethane (d5) is preferably a linear polyurethane. The polyurethane (d5) is obtained, for example, by reacting a polyol component (a polyether polyol, a polyester polyol, a polycarbonate polyol, or the like), an organic isocyanate component (an aromatic diisocyanate, an aliphatic (including alicyclic) diisocyanate, or the like), and, if necessary, a chain extender (an aliphatic (including alicyclic) diol, or the like). Each of the polyol component and the organic isocyanate component may be used alone, or may be used in combination of two or more thereof.

The polyurethane (d5) is preferably an aliphatic polyurethane from the viewpoint of obtaining the excellent Charpy impact strength. The aliphatic polyurethane is preferably obtained, for example, by reacting a polyol component containing a polycarbonate polyol with an isocyanate component containing an aliphatic diisocyanate.

The polyurethane (d5) may be obtained by reacting a polyol component with an organic isocyanate component in a manner that a value of an NCO/OH ratio in a raw material in a synthesis of polyurethane is within a range of 0.90 to 1.5. The polyurethane (d5) is obtained by a known method such as a one-shot method, a prepolymerization method or the like.

Examples of the commercially available product of the polyurethane (d5) include "Estane" (registered trademark) manufactured by Lubrizol Corporation, "Elastollan" (registered trademark) manufactured by BASF and "Desmopan" (registered trademark) manufactured by Bayer, or the like.

—Polyester (d6): Component (d6)—

The polyester (d6) is not particularly limited as long as it is a thermoplastic elastomer, and examples thereof include a known polyester. The polyester (d6) is preferably an aromatic polyester from the viewpoint of obtaining the excellent Charpy impact strength. In the exemplary embodiment, the aromatic polyester represents a polyester having an aromatic ring in the structure thereof.

Examples of the polyester (d6) include a polyester copolymer (polyether ester, polyester ester, or the like). Specific examples include a polyester copolymer having a hard segment including a polyester unit and a soft segment including a polyester unit; a polyester copolymer having a hard segment including a polyester unit and a soft segment including a polyether unit; and a polyester copolymer having a hard segment including a polyester unit and a soft segment including a polyether unit and a polyester unit. The mass ratio (hard segment/soft segment) of the hard segment to the soft segment in the polyester copolymer is preferably, for example, 20/80 to 80/20. The polyester unit constituting the hard segment and the polyester unit and the polyether unit constituting the soft segment may be either aromatic or aliphatic (including alicyclic).

The polyester copolymer as the polyester (d6) may be obtained by a known method. The polyester copolymer is preferably a linear polyester copolymer. The polyester copolymer is obtained, for example, by esterifying or transesterifying a dicarboxylic acid component having 4 to 20 carbon atoms, a diol component having 2 to 20 carbon atoms and a polyalkylene glycol component having a number average molecular weight of 300 to 20000 (containing an alkylene oxide adduct of polyalkylene glycols) and by polycondensating an oligomer produced by esterifying or transesterifying components thereof. In addition, examples of the esterification or transesterification method include a method using a dicarboxylic acid component having 4 to 20 carbon atoms, a diol component having 2 to 20 carbon atoms, and an aliphatic polyester component having a number average molecular weight of 300 to 20000. The dicarboxylic acid component is an aromatic or aliphatic dicarboxylic acid or an ester derivative thereof, the diol component is an aromatic or aliphatic diol, and the polyalkylene glycol component is an aromatic or aliphatic polyalkylene glycol.

Of these, it is preferable to use a dicarboxylic acid component having an aromatic ring as the dicarboxylic acid component of the polyester copolymer, from the viewpoint of obtaining the excellent Charpy impact strength. It is preferable to use an aliphatic diol component and an aliphatic polyalkylene glycol component as the diol component and the polyalkylene glycol component, respectively.

Examples of the commercially available product of the polyester (d6) include "PELPRENE" (registered trademark) manufactured by Toyobo Co., Ltd. and "Hytrel" (registered trademark) manufactured by DU PONT-TORAY CO., LTD.

[Content or Content Ratio of Components (A) to (D)]

It is preferable that in the resin composition according to the exemplary embodiment preferably, the content or content ratio (all on a mass basis) of each component is in the following range from the viewpoint of easily obtaining the effect of improving the toughness by the addition of the component (C).

The abbreviation of each component is as follows.
Component (A)=cellulose acylate (A)
Component (B)=cardanol compound (B)
Component (C)=compound (C)
Component (D)=thermoplastic elastomer (D)

The content of the component (A) in the resin composition according to the exemplary embodiment is preferably 50% by mass or more, more preferably 60% by mass or more, and still more preferably 70% by mass or more, based on the total amount of the resin composition.

The content of the component (B) in the resin composition according to the exemplary embodiment is preferably from 1% by mass to 25% by mass, more preferably from 3% by mass to 20% by mass, and still more preferably from 5% by mass to 15% by mass, based on the total amount of the resin composition.

The content of the component (C) in the resin composition according to the exemplary embodiment is preferably from 0.01 mass % to 5 mass %, more preferably from 0.05 mass % to 2 mass %, and still more preferably from 0.1 mass % to 1 mass %, based on the total amount of the resin composition.

The content of the component (D) in the resin composition according to the exemplary embodiment is preferably from 1% by mass to 20% by mass, more preferably from 3% by mass to 15% by mass, and still more preferably from 5% by mass to 10% by mass, based on the total amount of the resin composition.

The percentage of the component (C) to the total amount of the cellulose acylate (A), the cardanol compound (B) and the compound (C) is preferably from 0.05% by mass to 5% by mass, more preferably from 0.1% by mass to 5% by mass, and still more preferably from 0.1% by mass to 1% by mass.

The content ratio of the component (B) to the component (A) is preferably $0.03 \leq (B)/(A) \leq 0.3$, more preferably $0.05 \leq (B)/(A) \leq 0.2$, and still more preferably $0.07 \leq (B)/(A) \leq 0.15$.

The content ratio of the component (A) to the component (D) is preferably $0.025 \leq (D)/(A) \leq 0.3$, more preferably $0.05 \leq (D)/(A) \leq 0.2$, and still more preferably $0.06 \leq (D)/(A) \leq 0.15$.

[Other Components]

The resin composition according to the exemplary embodiment may contain other components.

Examples of other components include: a plasticizer, a flame retardant, a compatibilizer, a releasing agent, a light fastness agent, a weathering agent, a colorant, a pigment, a modifier, a drip inhibitor, an antistatic agent, a hydrolysis inhibitor, a filler, a reinforcing agent (such as glass fiber, carbon fiber, talc, clay, mica, glass flake, milled glass, glass beads, crystalline silica, alumina, silicon nitride, aluminum nitride, and boron nitride), an acid acceptor for preventing acetic acid from releasing (oxides such as magnesium oxide and aluminum oxide; metal hydroxides such as magnesium hydroxide, calcium hydroxide, aluminum hydroxide and hydrotalcite; calcium carbonate; talc; or the like), a reactive trapping agent (such as an epoxy compound, an acid anhydride compound, and carbodiimide), or the like.

The content of other components is preferably from 0% by mass to 5% by mass with respect to the total amount of the resin composition. Here, "0% by mass" means not containing other components in the resin composition.

Examples of the plasticizer include an ester compound, camphor, a metal soap, a polyol, polyalkylene oxide, or the like. The plasticizer is preferably an ester compound from the viewpoint of obtaining the impact resistance of the resin molded article. The plasticizer may be used alone, or may be used in combination of two or more thereof.

Examples of the ester compound contained as a plasticizer in the resin composition according to the exemplary embodiment include adipates, citrates, sebacates, azelates, phthalates, acetates, dibasiates, phosphates, condensed phosphates, glycol esters (e.g., glycol benzoate), modified products of fatty acid esters (e.g., epoxidized fatty acid esters), or the like. Examples of the above ester include a monoester, a diester, a triester, and a polyester. Of these, dicarboxylic diesters (e.g., adipic acid diester, sebacic acid diester, azelaic acid diester, and phthalic acid diester) are preferred.

The plasticizer is preferably an adipate ester. The adipate ester may have high affinity with the cellulose acylate (A), and disperse in a state close to uniformity to the cellulose acylate (A), thereby further improving the thermal fluidity as compared with another plasticizer.

A mixture of an adipate ester and other components may be used as the adipate ester. Examples of the commercially available product of the mixture include Daifatty 101 manufactured by DAIHACHI CHEMICAL INDUSTRY CO., LTD.

Examples of the fatty acid esters such as citric acid ester, sebacic acid ester, azelaic acid ester, phthalic acid ester, and acetic acid ester include an ester of a fatty acid and an alcohol. Examples of the alcohol include: monohydric alcohols such as methanol, ethanol, propanol, butanol, and 2-ethylhexanol; polyhydric alcohols such as glycerin, a polyglycerol (diglycerin or the like), pentaerythritol, ethylene glycol, diethylene glycol, propylene glycol, butylene glycol, trimethylolpropane, trimethylol ethane, and a sugar alcohol; or the like.

Examples of the glycol in the glycol benzoate include ethylene glycol, diethylene glycol, propylene glycol, or the like.

The epoxidized fatty acid ester is an ester compound having a structure (that is, oxacyclopropane) in which an unsaturated carbon-carbon bond of an unsaturated fatty acid ester is epoxidized. Examples of the epoxidized fatty acid ester include an ester of a fatty acid and an alcohol in which part or the entire unsaturated carbon-carbon bond in an unsaturated fatty acid (e.g., oleic acid, palmitoleic acid, vaccenic acid, linoleic acid, linolenic acid, and nervonic acid) is epoxidized. Examples of the alcohol include: monohydric alcohols such as methanol, ethanol, propanol, butanol, and 2-ethylhexanol; polyhydric alcohols such as glycerin, a polyglycerol (diglycerin or the like), pentaerythritol, ethylene glycol, diethylene glycol, propylene glycol, butylene glycol, trimethylolpropane, trimethylol ethane, and a sugar alcohol; or the like.

The ester compound contained as a plasticizer in the resin composition according to the exemplary embodiment preferably has a molecular weight (or a weight average molecular weight) of 200 to 2000, more preferably 250 to 1500, and still more preferably 280 to 1000. The weight average molecular weight of the ester compound is not particularly limited, and is a value measured according to the method of measuring the weight average molecular weight of the cellulose acylate (A).

The resin composition according to the exemplary embodiment may contain other resins in addition to the component (A), the component (B), the component (C) and the component (D). However, in the case of containing other resins, the content of other resins based on the total amount of the resin composition is preferably 5% by mass or less, and is preferably less than 1% by mass. It is more preferable to not contain other resins in the resin composition (that is, 0% by mass).

Examples of other resins include thermoplastic resins known in the related art, and specifically include: a polycarbonate resin; a polypropylene resin; a polyester resin; a polyolefin resin; a polyester carbonate resin; a polyphenylene ether resin; a polyphenylene sulfide resin; a polysulfone resin; a polyether sulfone resin; a polyarylene resin; a polyether imide resin; a polyacetal resin; a polyvinyl acetal resin; a polyketone resin; a polyether ketone resin; a polyether ether ketone resin; a polyaryl ketone resin; a polyether nitrile resin; a liquid crystal resin; a polybenzimidazole resin; a polyparabanic acid resin; a vinyl polymer or copolymer obtained by polymerizing or copolymerizing one or more vinyl monomers selected from the group consisting of an aromatic alkenyl compound, a methacrylic acid ester, an acrylic acid ester, and a vinyl cyanide compound; a diene-aromatic alkenyl compound copolymer; a vinyl cyanide-diene-aromatic alkenyl compound copolymer; an aromatic alkenyl compound-diene-vinyl cyanide-N-phenyl maleimide copolymer; a vinyl cyanide-(ethylene-diene-propylene (EPDM))-aromatic alkenyl compound copolymer; a vinyl chloride resin; a chlorinated vinyl chloride resin; or the like. The above resins may be used alone, or may be used in combination of two or more thereof.

[Method for Producing Resin Composition]

Examples of the method for producing the resin composition according to the exemplary embodiment include: a method for mixing and melt-kneading at least one of the component (A), the component (B), the component (C) and the component (D), and, if necessary, other components; a method for dissolving at least one of the component (A), the component (B), the component (C) and the component (D), and, if necessary, other components in a solvent; or the like. Here, the melt-kneading means is not particularly limited, and examples thereof include a twin-screw extruder, a Henschel mixer, a Banbury mixer, a single screw extruder, a multi-screw extruder, a co-kneader or the like.

<Resin Molded Article>

The resin molded article according to the exemplary embodiment contains the resin composition according to the exemplary embodiment. That is, the resin molded article according to the exemplary embodiment has the same composition as the resin composition according to the exemplary embodiment.

The method for forming the resin molded article according to the exemplary embodiment is preferably the injection molding from the viewpoint of obtaining a high degree of freedom of shape. Therefore, the resin molded article according to the exemplary embodiment is preferably an injection molded article obtained by the injection molding, from the viewpoint of obtaining a high degree of freedom of shape.

The cylinder temperature during the injection molding of the resin molded article according to the exemplary embodiment is, for example, 160° C. to 280° C., and preferably 180° C. to 240° C. The mold temperature during the injection molding of the resin molded article according to the exemplary embodiment is, for example, 40° C. to 90° C., and more preferably 40° C. to 60° C.

The injection molding of the resin molded article according to the exemplary embodiment may be performed, for example, by using commercial devices such as NEX 500 manufactured by NISSEI PLASTIC INDUSTRIAL CO., LTD., NEX 150 manufactured by NISSEI PLASTIC INDUSTRIAL CO., LTD., NEX 7000 manufactured by NISSEI PLASTIC INDUSTRIAL CO., LTD., PNX 40 manufactured by NISSEI PLASTIC INDUSTRIAL CO., LTD., and SE50D manufactured by Sumitomo Heavy Industries, Ltd.

The molding method for obtaining the resin molded article according to the exemplary embodiment is not limited to the above injection molding, and injection molding, extrusion molding, blow molding, hot press molding, calender molding, coating molding, cast molding, dipping molding, vacuum molding, transfer molding or the like may also be applied.

The resin molded article according to the exemplary embodiment is suitably used for applications such as electronic and electrical equipment, office equipment, household electric appliances, automotive interior materials, toys, containers, or the like. Specific applications of the resin molded article according to the exemplary embodiment include: casings of electronic/electric devices or household electric appliances; various parts of electronic/electric devices or home electric appliances; interior parts of automobiles; block assembled toys; plastic model kits; CD-ROM or DVD storage cases; dishware; beverage bottles; food trays; wrapping materials; films; sheets; or the like.

EXAMPLES

Hereinafter, the resin composition and the resin molded article according to the exemplary embodiment will be described in more detail by means of examples. Materials, amounts, ratios, processing procedures, or the like shown in the following examples may be appropriately changed without departing from the gist of the present disclosure. Therefore, the resin composition and the resin molded article according to the exemplary embodiment should not be interpreted restrictively by the following specific examples.

<Preparation of Each Material>

The following materials were prepared.

[Cellulose Acylate (A)]

CA1: Eastman Chemical "CAP 482-20", cellulose acetate propionate, having a weight-average degree of polymerization of 716, a degree of acetyl group substitution of 0.18 and a degree of propionyl group substitution of 2.49.

CA2: Eastman Chemical "CAP 482-0.5", cellulose acetate propionate, having a weight-average degree of polymerization of 189, a degree of acetyl group substitution of 0.18 and a degree of propionyl group substitution of 2.49.

CA3: Eastman Chemical "CAP 504-0.2", cellulose acetate propionate, having a weight-average degree of polymerization of 133, a degree of acetyl group substitution of 0.04 and a degree of propionyl group substitution of 2.09.

CA4: Eastman Chemical "CAB 171-15", cellulose acetate butyrate, having a weight-average degree of polymerization of 754, a degree of acetyl group substitution of 2.07 and a degree of butyryl group substitution of 0.73.

CA5: Eastman Chemical "CAB 381-20", cellulose acetate butyrate, having a weight-average degree of polymerization of 890, a degree of acetyl group substitution of 1.05 and a degree of butyryl group substitution of 1.74.

CA6: Eastman Chemical "CAB 500-5", cellulose acetate butyrate, having a weight-average degree of polymerization of 625, a degree of acetyl group substitution of 0.17 and a degree of butyryl group substitution of 2.64.

CA7: Daicel "L50", diacetyl cellulose, having a weight-average degree of polymerization of 570.

CA8: Daicel "LT-35", triacetyl cellulose, having a weight-average degree of polymerization of 385.

RC2: Eastman Chemical "Treva GC6021", cellulose acetate propionate, having a weight-average degree of polymerization of 716, a degree of acetyl group substitution of 0.18 and a degree of propionyl group substitution of 2.49. The product contains 3% by mass to 10% by mass of a chemical substance corresponding to the component (D).

CA1 satisfied the following (2), (3) and (4). CA2 satisfied the following (4). (2) When measured by the GPC method using tetrahydrofuran as a solvent, the weight average molecular weight (Mw) in terms of polystyrene is 160,000 to 250,000, a ratio Mn/Mz of a number average molecular weight (Mn) in terms of polystyrene to a Z average molecular weight (Mz) in terms of polystyrene is 0.14 to 0.21, and a ratio Mw/Mz of a weight average molecular weight (Mw) in terms of polystyrene to the Z average molecular weight (Mz) in terms of polystyrene is 0.3 to 0.7. (3) When measured with a Capirograph at a condition of 230° C. according to ISO 11443:1995, a ratio $\eta1/\eta2$ of a viscosity $\eta1$ (Pa·s) at a shear rate of 1216 (/sec) to a viscosity $\eta2$ (Pa·s) at a shear rate of 121.6 (/sec) is 0.1 to 0.3. (4) When a small square plate test piece (D11 test piece specified by JIS K7139:2009, 60 mm×60 mm, thickness 1 mm) obtained by the injection molding of the CAP is allowed to stand in an atmosphere at a temperature of 65° C. and a relative humidity of 85% for 48 hours, both an expansion coefficient in an MD direction and an expansion coefficient in a TD direction are 0.4% to 0.6%.

[Cardanol Compound (B)]

CN1: Cardolite "NX-2026", cardanol, having a molecular weight of 298 to 305.

CN2: Cardolite "Ultra LITE 2023", cardanol (which is acidified to stabilize the color), having a molecular weight of 298 to 305.

CN3: Cardolite "Ultra LITE 2020", hydroxyethylated cardanol, having a molecular weight of 343 to 349.

CN4: Cardolite "GX-5170", hydroxyethylated cardanol, having a molecular weight of 827 to 833.

CN5: Cardolite "Ultra LITE 513", glycidyl ether of cardanol, having a molecular weight of 354 to 361.

CN6: Cardolite "NC-514S", cardanol-derived bifunctional epoxy compound, having a molecular weight of 534 to 537.

CN7: Cardolite "NC-547", cardanol-derived trifunctional epoxy compound, having a molecular weight of 1087 to 1106.

[Compound (C)]
- ST1: BASF "Irganox B225", a mixture of pentaerythritol tetraki s(3-(3',5'-di-t-butyl-4'-hydroxyphenyl)propionate) and tri s(2,4-di-t-butylphenyl) phosphite. A mixture of a compound represented by the General Formula (HP1) and a compound represented by the General Formula (P1).
- ST2: BASF "Irganox 1010", pentaerythritol tetrakis(3-(3',5'-di-t-butyl-4'-hydroxyphenyl)propionate). A compound represented by the General Formula (HP1).
- ST3: BASF "Irganox 245", ethylenebis(oxyethylene) bis [3-(3-tert-butyl-4-hydroxy-5-methylphenyl)propionate]. A compound represented by the General Formula (HP1).
- ST4: ADEKA "ADK STAB AO-80", 2,2'-dimethyl-2,2'-(2,4,8,10-tetraoxaspiro[5.5]undecane-3,9-diyl)dipropane-1,1'-diyl bis[3-(3-tert-butyl-4-hydroxy-5-methylphenyl) propanoate]. A compound represented by the General Formula (HP1).
- ST5: BASF "Irganox E201", α-tocopherol. A compound represented by the General Formula (T1).
- ST6: BASF "Irgafos 168", tris(2,4-di-t-butylphenyl) phosphite. A compound represented by the General Formula (P1).
- ST7: BASF "Irgastab FS 301", a mixture of N,N-dioctadecylhydroxylamine and tris(2,4-di-t-butylphenyl) phosphite. A mixture of a compound represented by the General Formula (HA1) and a compound represented by the General Formula (P1).
- ST8: Sumitomo Chemical "Sumilizer GP", 6-[3-(3-t-butyl-4-hydroxy-5-methylphenyl)propoxy]-2,4,8,10-tetra-t-butyl dibenzo[d,f][1,3,2]dioxaphosphepin. A compound represented by the General Formula (P3).
- ST9: Sumitomo Chemical "Sumilizer GM", 2-t-butyl-6-(3-t-butyl-2-hydroxy-5-methylbenzyl)-4-methylphenyl acrylate. A compound represented by the General Formula (HP2).
- ST10: Sumitomo Chemical "Sumilizer GS", 2-[1-(2-hydroxy-3,5-di-t-pentylphenyl)ethyl]-4,6-di-t-pentylphenyl acrylate. A compound represented by the General Formula (HP2).
- ST11: Sigma-Aldrich "bis(octadecyl) hydroxylamine", N,N-dioctadecylhydroxylamine. A compound represented by the General Formula (HA1).
- ST12: ADEKA "ADK STAB LA-52", a hindered amine compound. A comparative compound.

[Thermoplastic Elastomer (D)]
- EL1: Mitsubishi Chemical "METABLEN W-600A", core-shell structure polymer (d1), a polymer having a shell layer obtained by grafting and polymerizing "a methyl methacrylate homopolymer rubber" to "a copolymer rubber of 2-ethylhexyl acrylate and n-butyl acrylate" as a core layer, having an average primary particle diameter of 200 nm.
- EL2: Mitsubishi Chemical "METABLEN S-2006", core-shell structure polymer (d1), a polymer whose core layer contains a "silicone-acrylic rubber" and whose shell layer contains a "methyl methacrylate polymer", having an average primary particle diameter of 200 nm.
- EL3: Dow Chemical Japan "PARALOID EXL2315", core-shell structure polymer (d1), a polymer having a shell layer obtained by grafting and polymerizing a "methyl methacrylate polymer" to a "rubber whose main component is butyl polyacrylate" as a core layer and having an average primary particle diameter of 300 nm.
- EL4: Arkema "Lotryl 29 MA 03", olefin polymer (d2), an olefin polymer which is a copolymer of ethylene and methyl acrylate and contains 71% by mass of a structural unit derived from ethylene.
- EL5: Kaneka "Kane Ace B-564", an MBS resin, core-shell structure polymer (d3).
- EL6: Galata Chemicals (Artek) "Blendex 338", an ABS core shell, core-shell structure polymer (d3).
- EL7: Kraton Corporation "Kraton FG 1924G", styrene-ethylene-butadiene-styrene copolymer (d4).
- EL8: Lubrizol "Estane ALR 72A", polyurethane (d5).
- EL9: DU PONT-TORAY "Hytrel 3078", an aromatic polyester copolymer, polyester (d6).

[Others]
- PL1: DAIHACHI CHEMICAL INDUSTRY "Daifatty 101", an adipate ester-containing compound, having a molecular weight of 326 to 378.
- PE1: Nature Works "Ingeo 3001D", a polylactic acid.
- PM1: Asahi Kasei "DELPET 720V", polymethyl methacrylate.
- LB1: FUJIFILM Wako pure chemical "Stearyl Stearate", stearyl stearate.

<Production of Resin Composition and Injection Molding of Resin Molded Article>

Examples 1 to 57, Comparative Examples 1 to 33, and Reference Examples A to B

Kneading was performed with a twin-screw kneader (LTE 20-44, manufactured by labtech engineering) at the charged amounts and kneading temperatures shown in Tables 1 to 4 to obtain a pellet (resin composition). An ISO multipurpose test piece (dumbbell shaped, measurement part dimensions: width 10 mm and thickness 4 mm) and a small square plate test piece (D12 test piece specified by JIS K7139:2009, 60 mm×60 mm, thickness 2 mm) were molded with an injection molding machine (NEX 5001, manufactured by NISSEI PLASTIC INDUSTRIAL CO., LTD.) using the pellet at an injection peak pressure not exceeding 180 MPa and at the molding temperatures and the mold temperatures shown in Tables 1 to 4.

<Performance Evaluation on Resin Molded Article>

[Charpy Impact Strength]

Notch processing was applied to the center of the measurement part of the ISO multipurpose test piece (the remaining width of the measurement part was 8 mm) using a notch processing device (Notching tool A-4 type, manufactured by Toyo Seiki Seisaku-sho, Ltd.) to obtain a notched test piece.

The notched test piece was set on an impact test device (digital impact tester DG-UB type, manufactured by Toyo Seiki Seisaku-sho, Ltd.) and the Charpy impact strength ($kJ/m^2$) was measured using a 2 J hammer according to ISO 179-1:2010. The results are shown in Tables 1 to 4.

[Toughness (Impact Absorption Energy)]

The small square plate test piece was set on a drop-weight impact tester (CEAST 9310, manufactured by INSTRON), and a puncture impact test was performed according to ISO 6603-2:2000. The test conditions were set to a drop weight of 3.09 kg, a drop height of 0.70 m (falling energy of 21.21 J), and the impact force and impact energy were measured to obtain the impact absorption energy (J). The results are shown in Tables 1 to 4.

TABLE 1

| Items | (A) Type | (A) Amount | (B) Type | (B) Amount | (C) Type | (C) Amount | (C) Type | (C) Amount | (D) Type | (D) Amount | Others Type | Others Amount | Others Type | Others Amount |
|---|---|---|---|---|---|---|---|---|---|---|---|---|---|---|
| Reference Example A | CA1 | 88 | | | | | | | | | PL1 | 12 | | |
| Reference Example B | CA1 | 88 | | | ST1 | 0.5 | | | | | PL1 | 12 | | |
| Comparative Example 1 | CA1 | 88 | CN1 | 12 | | | | | | | | | | |
| Comparative Example 2 | CA1 | 88 | CN1 | 12 | | | | | | | PE1 | 5 | | |
| Comparative Example 3 | CA1 | 91.5 | CN1 | 8.5 | | | | | EL1 | 7.5 | | | | |
| Comparative Example 4 | CA1 | 91.5 | CN1 | 8.5 | | | | | EL1 | 7.5 | PE1 | 5 | | |
| Comparative Example 5 | CA1 | 91.5 | CN1 | 8.5 | | | | | EL1 | 7.5 | PE1 | 5 | | |
| Comparative Example 6 | CA1 | 88 | CN1 | 12 | ST12 | 0.5 | | | | | | | | |
| Example 1 | CA1 | 88 | CN1 | 12 | ST1 | 0.5 | | | | | | | | |
| Example 2 | CA1 | 88 | CN1 | 12 | ST1 | 0.5 | | | | | PE1 | 5 | | |
| Example 3 | CA1 | 91.5 | CN1 | 8.5 | ST1 | 0.5 | | | EL1 | 7.5 | | | | |
| Example 4 | CA1 | 91.5 | CN1 | 8.5 | ST1 | 0.5 | | | EL1 | 7.5 | PE1 | 5 | | |
| Example 5 | CA1 | 91.5 | CN1 | 8.5 | ST1 | 0.5 | | | EL1 | 7.5 | PE1 | 5 | | |
| Example 6 | CA1 | 88 | CN1 | 12 | ST2 | 0.5 | | | | | | | | |
| Example 7 | CA1 | 88 | CN1 | 12 | ST3 | 0.5 | | | | | | | | |
| Example 8 | CA1 | 88 | CN1 | 12 | ST4 | 0.5 | | | | | | | | |
| Example 9 | CA1 | 88 | CN1 | 12 | ST5 | 0.5 | | | | | | | | |
| Example 10 | CA1 | 88 | CN1 | 12 | ST6 | 0.5 | | | | | | | | |
| Example 11 | CA1 | 88 | CN1 | 12 | ST7 | 0.5 | | | | | | | | |
| Example 12 | CA1 | 88 | CN1 | 12 | ST8 | 0.5 | | | | | | | | |
| Example 13 | CA1 | 88 | CN1 | 12 | ST9 | 0.5 | | | | | | | | |
| Example 14 | CA1 | 88 | CN1 | 12 | ST10 | 0.5 | | | | | | | | |
| Example 15 | CA1 | 88 | CN1 | 12 | ST11 | 0.5 | | | | | | | | |
| Example 16 | CA1 | 88 | CN1 | 12 | ST1 | 0.04 | ST5 | 0.04 | | | | | | |
| Example 17 | CA1 | 88 | CN1 | 12 | ST1 | 0.06 | ST5 | 0.06 | | | | | | |
| Example 18 | CA1 | 88 | CN1 | 12 | ST3 | 0.25 | ST6 | 0.25 | | | | | | |
| Example 19 | CA1 | 88 | CN1 | 12 | ST4 | 0.25 | ST6 | 0.25 | | | | | | |

| Items | Others Type | Others Amount | Others Type | Others Amount | C/A + B + C [%] | Kneading temperature [°C] | Molding temperature [°C] | Mold temperature [°C] | Charpy impact strength [kJ/m²] | Impact absorption energy [J] |
|---|---|---|---|---|---|---|---|---|---|---|
| Reference Example A | | | | | — | 200 | 200 | 40 | 18.5 | 14 |
| Reference Example B | | | | | — | 200 | 200 | 40 | 18.3 | 14 |
| Comparative Example 1 | | | | | 0 | 200 | 200 | 40 | 17.4 | 2 |
| Comparative Example 2 | PM1 | 5 | | | 0 | 200 | 200 | 40 | 15.8 | 2 |
| Comparative Example 3 | | | | | 0 | 210 | 210 | 40 | 18.1 | 5 |
| Comparative Example 4 | PM1 | 5 | | | 0 | 210 | 210 | 40 | 17.7 | 5 |
| Comparative Example 5 | PM1 | 5 | LB1 | 2 | 0 | 210 | 210 | 40 | 18.8 | 5 |
| Comparative Example 6 | | | | | 0.5 | 200 | 200 | 40 | 17.2 | 2 |
| Example 1 | | | | | 0.5 | 200 | 200 | 40 | 17.5 | 15 |
| Example 2 | PM1 | 5 | | | 0.5 | 200 | 200 | 40 | 15.8 | 12 |
| Example 3 | | | | | 0.5 | 210 | 210 | 40 | 18.4 | 20 |
| Example 4 | PM1 | 5 | | | 0.5 | 210 | 210 | 40 | 18.0 | 20 |
| Example 5 | PM1 | 5 | LB1 | 2 | 0.5 | 210 | 210 | 40 | 18.6 | 19 |
| Example 6 | | | | | 0.5 | 200 | 200 | 40 | 17.5 | 15 |
| Example 7 | | | | | 0.5 | 200 | 200 | 40 | 17.4 | 15 |
| Example 8 | | | | | 0.5 | 200 | 200 | 40 | 17.5 | 15 |
| Example 9 | | | | | 0.5 | 200 | 200 | 40 | 17.0 | 9 |
| Example 10 | | | | | 0.5 | 200 | 200 | 40 | 17.3 | 15 |
| Example 11 | | | | | 0.5 | 200 | 200 | 40 | 17.4 | 7 |
| Example 12 | | | | | 0.5 | 200 | 200 | 40 | 17.4 | 15 |
| Example 13 | | | | | 0.5 | 200 | 200 | 40 | 17.5 | 15 |
| Example 14 | | | | | 0.5 | 200 | 200 | 40 | 17.6 | 14 |
| Example 15 | | | | | 0.5 | 200 | 200 | 40 | 17.4 | 12 |
| Example 16 | | | | | 0.08 | 200 | 200 | 40 | 17.5 | 7 |

TABLE 1-continued

|  |  |  |  |  |  |  |
|---|---|---|---|---|---|---|
| Example 17 |  | 0.12 | 200 | 200 | 40 | 17.6 | 13 |
| Example 18 |  | 0.5 | 200 | 200 | 40 | 17.3 | 15 |
| Example 19 |  | 0.5 | 200 | 200 | 40 | 17.2 | 15 |

TABLE 2

| Items | (A) Type | (A) Amount | (B) Type | (B) Amount | (C) Type | (C) Amount | (C) Type | (C) Amount | (D) Type | (D) Amount | Others Type | Others Amount |
|---|---|---|---|---|---|---|---|---|---|---|---|---|
| Comparative Example 7 | CA1 | 88 | CN5 | 12 |  |  |  |  |  |  |  |  |
| Comparative Example 8 | CA1 | 88 | CN5 | 12 |  |  |  |  |  |  | PE1 | 5 |
| Comparative Example 9 | CA1 | 91.5 | CN5 | 8.5 |  |  |  |  | EL1 | 7.5 |  |  |
| Comparative Example 10 | CA1 | 91.5 | CN5 | 8.5 |  |  |  |  | EL1 | 7.5 | PE1 | 5 |
| Comparative Example 11 | CA1 | 91.5 | CN5 | 8.5 |  |  |  |  | EL1 | 7.5 | PE1 | 5 |
| Comparative Example 12 | CA1 | 88 | CN5 | 12 | ST12 | 0.5 |  |  |  |  |  |  |
| Example 20 | CA1 | 88 | CN5 | 12 | ST1 | 0.5 |  |  |  |  |  |  |
| Example 21 | CA1 | 88 | CN5 | 12 | ST1 | 0.5 |  |  |  |  | PE1 | 5 |
| Example 22 | CA1 | 91.5 | CN5 | 8.5 | ST1 | 0.5 |  |  | EL1 | 7.5 |  |  |
| Example 23 | CA1 | 91.5 | CN5 | 8.5 | ST1 | 0.5 |  |  | EL1 | 7.5 | PE1 | 5 |
| Example 24 | CA1 | 91.5 | CN5 | 8.5 | ST1 | 0.5 |  |  | EL1 | 7.5 | PE1 | 5 |
| Example 25 | CA1 | 88 | CN5 | 12 | ST2 | 0.5 |  |  |  |  |  |  |
| Example 26 | CA1 | 88 | CN5 | 12 | ST3 | 0.5 |  |  |  |  |  |  |
| Example 27 | CA1 | 88 | CN5 | 12 | ST4 | 0.5 |  |  |  |  |  |  |
| Example 28 | CA1 | 88 | CN5 | 12 | ST5 | 0.5 |  |  |  |  |  |  |
| Example 29 | CA1 | 88 | CN5 | 12 | ST6 | 0.5 |  |  |  |  |  |  |
| Example 30 | CA1 | 88 | CN5 | 12 | ST7 | 0.5 |  |  |  |  |  |  |
| Example 31 | CA1 | 88 | CN5 | 12 | ST8 | 0.5 |  |  |  |  |  |  |
| Example 32 | CA1 | 88 | CN5 | 12 | ST9 | 0.5 |  |  |  |  |  |  |
| Example 33 | CA1 | 88 | CN5 | 12 | ST10 | 0.5 |  |  |  |  |  |  |
| Example 34 | CA1 | 88 | CN5 | 12 | ST11 | 0.5 |  |  |  |  |  |  |
| Example 35 | CA1 | 88 | CN5 | 12 | ST3 | 0.25 | ST6 | 0.25 |  |  |  |  |
| Example 36 | CA1 | 88 | CN5 | 12 | ST4 | 0.25 | ST6 | 0.25 |  |  |  |  |

| Items | Others Type | Others Amount | Others Type | Others Amount | C/A + B + C [%] | Kneading temperature [° C.] | Molding temperature [° C.] | Mold temperature [° C.] | Charpy impact strength [kJ/m²] | Impact absorption energy [J] |
|---|---|---|---|---|---|---|---|---|---|---|
| Comparative Example 7 |  |  |  |  | 0 | 200 | 200 | 40 | 17.5 | 2 |
| Comparative Example 8 | PM1 | 5 |  |  | 0 | 200 | 200 | 40 | 16.2 | 2 |
| Comparative Example 9 |  |  |  |  | 0 | 210 | 210 | 40 | 17.7 | 5 |
| Comparative Example 10 | PM1 | 5 |  |  | 0 | 210 | 210 | 40 | 18.0 | 5 |
| Comparative Example 11 | PM1 | 5 | LB1 | 2 | 0 | 210 | 210 | 40 | 18.5 | 5 |
| Comparative Example 12 |  |  |  |  | 0.5 | 200 | 200 | 40 | 17.4 | 2 |
| Example 20 |  |  |  |  | 0.5 | 200 | 200 | 40 | 17.6 | 15 |
| Example 21 | PM1 | 5 |  |  | 0.5 | 200 | 200 | 40 | 16.1 | 13 |
| Example 22 |  |  |  |  | 0.5 | 210 | 210 | 40 | 18.0 | 20 |
| Example 23 | PM1 | 5 |  |  | 0.5 | 210 | 210 | 40 | 17.9 | 20 |
| Example 24 | PM1 | 5 | LB1 | 2 | 0.5 | 210 | 210 | 40 | 18.4 | 20 |
| Example 25 |  |  |  |  | 0.5 | 200 | 200 | 40 | 17.3 | 15 |
| Example 26 |  |  |  |  | 0.5 | 200 | 200 | 40 | 17.5 | 15 |
| Example 27 |  |  |  |  | 0.5 | 200 | 200 | 40 | 17.6 | 15 |
| Example 28 |  |  |  |  | 0.5 | 200 | 200 | 40 | 17.4 | 7 |
| Example 29 |  |  |  |  | 0.5 | 200 | 200 | 40 | 17.2 | 14 |
| Example 30 |  |  |  |  | 0.5 | 200 | 200 | 40 | 17.5 | 6 |
| Example 31 |  |  |  |  | 0.5 | 200 | 200 | 40 | 17.5 | 14 |
| Example 32 |  |  |  |  | 0.5 | 200 | 200 | 40 | 17.4 | 14 |
| Example 33 |  |  |  |  | 0.5 | 200 | 200 | 40 | 17.7 | 15 |
| Example 34 |  |  |  |  | 0.5 | 200 | 200 | 40 | 17.7 | 7 |

TABLE 2-continued

| | | | | | | |
|---|---|---|---|---|---|---|
| Example 35 | 0.5 | 200 | 200 | 40 | 17.4 | 15 |
| Example 36 | 0.5 | 200 | 200 | 40 | 17.3 | 15 |

TABLE 3

| Items | Materials (amount is parts by mass) |||||||||||| Kneading temperature [° C.] | Molding temperature [° C.] | Mold temperature [° C.] | Charpy impact strength [kJ/m²] | Impact absorption energy [J] |
| | (A) || (B) || (C) || (D) || Others || Others || | | | | |
| | Type | Amount | Type | Amount | Type | Amount | Type | Amount | Type | Amount | Type | Amount | C/A + B + C [%] | | | | | |
| Comparative Example 13 | CA2 | 88 | CN1 | 12 | | | | | | | | | 0 | 200 | 200 | 40 | 16.4 | 1 |
| Comparative Example 14 | CA3 | 88 | CN1 | 12 | | | | | | | | | 0 | 200 | 200 | 40 | 16.4 | 1 |
| Comparative Example 15 | CA4 | 88 | CN1 | 12 | | | | | | | | | 0 | 220 | 210 | 40 | 14.6 | 5 |
| Comparative Example 16 | CA5 | 88 | CN1 | 12 | | | | | | | | | 0 | 200 | 200 | 40 | 17.2 | 5 |
| Comparative Example 17 | CA6 | 88 | CN1 | 12 | | | | | | | | | 0 | 200 | 200 | 40 | 18.0 | 5 |
| Comparative Example 18 | CA7 | 75 | CN1 | 25 | | | | | | | | | 0 | 230 | 230 | 40 | 11.3 | 2 |
| Comparative Example 19 | CA8 | 75 | CN1 | 25 | | | | | | | | | 0 | 250 | 250 | 60 | 9.9 | 2 |
| Comparative Example 20 | RC2 | 100 | CN1 | 5 | | | | | Containing RC2 derivate | | | | 0 | 220 | 220 | 40 | 18.1 | 5 |
| Example 37 | CA2 | 88 | CN1 | 12 | ST1 | 0.5 | | | | | | | 0.5 | 200 | 200 | 40 | 16.2 | 15 |
| Example 38 | CA3 | 88 | CN1 | 12 | ST1 | 0.5 | | | | | | | 0.5 | 200 | 200 | 40 | 16.1 | 13 |
| Example 39 | CA4 | 88 | CN1 | 12 | ST1 | 0.5 | | | | | | | 0.5 | 220 | 210 | 40 | 14.6 | 13 |
| Example 40 | CA5 | 88 | CN1 | 12 | ST1 | 0.5 | | | | | | | | | | | | |
| Example 41 | CA6 | 88 | CN1 | 12 | ST1 | 0.5 | | | | | | | | | | | | |
| Example 42 | CA7 | 75 | CN1 | 25 | ST1 | 0.5 | | | | | | | | | | | | |
| Example 43 | CA8 | 75 | CN1 | 25 | ST1 | 0.5 | | | | | | | | | | | | |
| Example 44 | RC2 | 100 | CN1 | 5 | ST1 | 0.5 | | | Containing RC2 derivate | | | | | | | | | |
| Comparative Example 21 | CA1 | 88 | CN2 | 12 | | | | | | | | | | | | | | |
| Comparative Example 22 | CA1 | 88 | CN3 | 12 | | | | | | | | | | | | | | |
| Comparative Example 23 | CA1 | 88 | CN4 | 12 | | | | | | | | | | | | | | |
| Comparative Example 24 | CA1 | 88 | CN6 | 12 | | | | | | | | | | | | | | |
| Comparative Example 25 | CA1 | 88 | CN7 | 12 | | | | | | | | | | | | | | |
| Example 45 | CA1 | 88 | CN2 | 12 | ST1 | 0.5 | | | | | | | | | | | | |
| Example 46 | CA1 | 88 | CN3 | 12 | ST1 | 0.5 | | | | | | | | | | | | |
| Example 47 | CA1 | 88 | CN4 | 12 | ST1 | 0.5 | | | | | | | | | | | | |
| Example 48 | CA1 | 88 | CN6 | 12 | ST1 | 0.5 | | | | | | | | | | | | |
| Example 49 | CA1 | 88 | CN7 | 12 | ST1 | 0.5 | | | | | | | | | | | | |

TABLE 3-continued

| | | | | | | |
|---|---|---|---|---|---|---|
| Example 40 | | 0.5 | 200 | 200 | 40 | 17.4 | 15 |
| Example 41 | | 0.5 | 200 | 200 | 40 | 18.2 | 17 |
| Example 42 | | 0.5 | 230 | 230 | 40 | 11.5 | 5 |
| Example 43 | | 0.5 | 250 | 250 | 60 | 9.7 | 4 |
| Example 44 | | >0.47 | 220 | 220 | 40 | 18.2 | 13 |
| Comparative Example 21 | | 0 | 200 | 200 | 40 | 17.6 | 2 |
| Comparative Example 22 | | 0 | 200 | 200 | 40 | 18.1 | 2 |
| Comparative Example 23 | | 0 | 200 | 200 | 40 | 17.3 | 1 |
| Comparative Example 24 | | 0 | 210 | 210 | 40 | 14.5 | 1 |
| Comparative Example 25 | | 0 | 220 | 220 | 40 | 12.7 | 1 |
| Example 45 | | 0.5 | 200 | 200 | 40 | 17.4 | 15 |
| Example 46 | | 0.5 | 200 | 200 | 40 | 18.2 | 15 |
| Example 47 | | 0.5 | 200 | 200 | 40 | 17.3 | 7 |
| Example 48 | | 0.5 | 210 | 210 | 40 | 14.2 | 5 |
| Example 49 | | 0.5 | 220 | 220 | 40 | 12.5 | 4 |

TABLE 4

| | Materials (amount is parts by mass) | | | | | | | | | | | |
|---|---|---|---|---|---|---|---|---|---|---|---|---|
| | (A) | | (B) | | (C) | | (D) | | | Others | | |
| Items | Type | Amount | Type | Amount | Type | Amount | Type | Amount | Type | Amount | Type | Amount |
| Comparative Example 26 | CA1 | 91.5 | CN1 | 8.5 | | | EL2 | 7.5 | | | | |
| Comparative Example 27 | CA1 | 91.5 | CN1 | 8.5 | | | EL3 | 7.5 | | | | |
| Comparative Example 28 | CA1 | 91.5 | CN1 | 8.5 | | | EL4 | 7.5 | | | | |
| Comparative Example 29 | CA1 | 91.5 | CN1 | 8.5 | | | EL5 | 7.5 | | | | |
| Comparative Example 30 | CA1 | 91.5 | CN1 | 8.5 | | | EL6 | 7.5 | | | | |
| Comparative Example 31 | CA1 | 91.5 | CN1 | 8.5 | | | EL7 | 7.5 | | | | |
| Comparative Example 32 | CA1 | 91.5 | CN1 | 8.5 | | | EL8 | 7.5 | | | | |
| Comparative Example 33 | CA1 | 91.5 | CN1 | 8.5 | | | EL9 | 7.5 | | | | |
| Example 50 | CA1 | 91.5 | CN1 | 8.5 | ST1 | 0.5 | EL2 | 7.5 | | | | |
| Example 51 | CA1 | 91.5 | CN1 | 8.5 | ST1 | 0.5 | EL3 | 7.5 | | | | |
| Example 52 | CA1 | 91.5 | CN1 | 8.5 | ST1 | 0.5 | EL4 | 7.5 | | | | |
| Example 53 | CA1 | 91.5 | CN1 | 8.5 | ST1 | 0.5 | EL5 | 7.5 | | | | |
| Example 51 | CA1 | 91.5 | CN1 | 8.5 | ST1 | 0.5 | EL6 | 7.5 | | | | |
| Example 55 | CA1 | 91.5 | CN1 | 8.5 | ST1 | 0.5 | EL7 | 7.5 | | | | |
| Example 56 | CA1 | 91.5 | CN1 | 8.5 | ST1 | 0.5 | EL8 | 7.5 | | | | |
| Example 57 | CA1 | 91.5 | CN1 | 8.5 | ST1 | 0.5 | EL9 | 7.5 | | | | |

| | Materials (amount is parts by mass) Others | | | | C/A + B + C [%] | Kneading temperature [° C.] | Molding temperature [° C.] | Mold temperature [° C.] | Charpy impact strength [kJ/m²] | Impact absorption energy [J] |
|---|---|---|---|---|---|---|---|---|---|---|
| Items | Type | Amount | Type | Amount | | | | | | |
| Comparative Example 26 | | | | | 0 | 210 | 210 | 40 | 18.0 | 5 |
| Comparative Example 27 | | | | | 0 | 210 | 210 | 40 | 18.0 | 5 |
| Comparative Example 28 | | | | | 0 | 210 | 210 | 40 | 16.7 | 4 |
| Comparative Example 29 | | | | | 0 | 210 | 210 | 40 | 16.5 | 4 |
| Comparative Example 30 | | | | | 0 | 210 | 210 | 40 | 15.7 | 3 |
| Comparative Example 31 | | | | | 0 | 210 | 210 | 40 | 16.6 | 5 |
| Comparative Example 32 | | | | | 0 | 210 | 210 | 40 | 16.4 | 5 |
| Comparative Example 33 | | | | | 0 | 210 | 210 | 40 | 16.0 | 4 |

TABLE 4-continued

| | | | | | | |
|---|---|---|---|---|---|---|
| Example 50 | 0.5 | 210 | 210 | 40 | 18.1 | 20 |
| Example 51 | 0.5 | 210 | 210 | 40 | 18.2 | 20 |
| Example 52 | 0.5 | 210 | 210 | 40 | 16.7 | 18 |
| Example 53 | 0.5 | 210 | 210 | 40 | 16.3 | 17 |
| Example 51 | 0.5 | 210 | 210 | 40 | 15.9 | 14 |
| Example 55 | 0.5 | 210 | 210 | 40 | 16.4 | 18 |
| Example 56 | 0.5 | 210 | 210 | 40 | 16.5 | 19 |
| Example 57 | 0.5 | 210 | 210 | 40 | 16.1 | 16 |

The foregoing description of the exemplary embodiments of the present invention has been provided for the purposes of illustration and description. It is not intended to be exhaustive or to limit the invention to the precise forms disclosed. Obviously, many modifications and variations will be apparent to practitioners skilled in the art. The embodiments were chosen and described in order to best explain the principles of the invention and its practical applications, thereby enabling others skilled in the art to understand the invention for various embodiments and with the various modifications as are suited to the particular use contemplated. It is intended that the scope of the invention be defined by the following claims and their equivalents.

What is claimed is:

1. A resin composition comprising:
   a cellulose acylate (A);
   a cardanol compound (B); and
   a compound (C) being at least one selected from the group consisting of a hindered phenol compound, a phosphite compound, and combinations thereof;
   wherein said hindered phenol compound comprises at least one compound selected from the group consisting of a compound represented by a general formula (HP1) and a compound represented by a general formula (HP2),

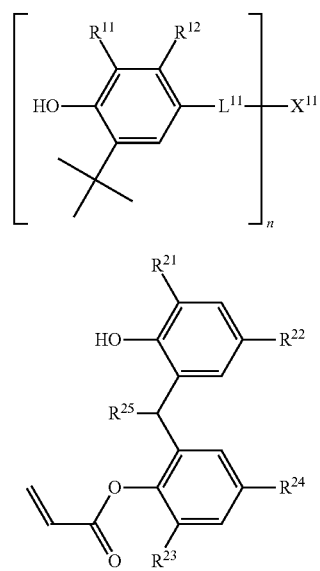

wherein $R^{11}$ and $R^{12}$ each independently represent a hydrogen atom or an alkyl group having 1 to 6 carbon atoms, $L^{11}$ represents a single bond or a divalent linking group, $X^{11}$ represents a single bond or an n-valent group, and n represents 1, 2, 3 or 4, and $R^{21}$, $R^{22}$, $R^{23}$, $R^{24}$, and $R^{25}$ each independently represent a hydrogen atom or an alkyl group having 1 to 6 carbon atoms; and wherein said phosphite compound comprises at least one selected from the group consisting of a compound represented by a general formula (P1), a compound represented by a general formula (P2), and a compound represented by a general formula (P3),

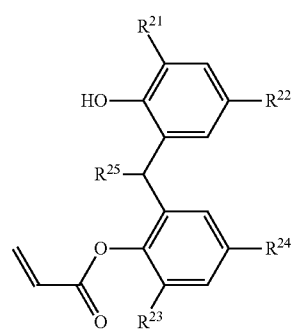

wherein $R^{41}$, $R^{42}$ and $R^{43}$ each independently represent a hydrogen atom or an alkyl group having 1 to 12 carbon atoms, $Y^{41}$ and $Y^{42}$ each independently represent an aliphatic hydrocarbon group, $n_{41}$ represents 1, 2 or 3, $m_{41}$ represents 0 or 1, m42 represents 0 or 1, and $n_{41}+m_{41}+m_{42}=3$, $R^{51}$, $R^{52}$, $R^{53}$, $R^{54}$, $R^{55}$, and $R^{56}$ each independently represent a hydrogen atom or an alkyl group having 1 to 12 carbon atoms, and $L^{51}$ represents a single bond or a divalent linking group and, $R^{61}$, $R^{62}$, $R^{63}$, $R^{64}$, $R^{65}$, and $R^{66}$ each independently represent a hydrogen atom or an alkyl group having 1 to 12 carbon atoms, and $L^{61}$ and $L^{62}$ each independently represent a single bond or a divalent linking group.

2. The resin composition according to claim 1, wherein the cellulose acylate (A) contains at least one selected from the group consisting of cellulose acetate propionate and cellulose acetate butyrate.

3. The resin composition according to claim 1, wherein the cardanol compound (B) contains a cardanol compound having a molecular weight of 500 or less.

4. The resin composition according to claim 1, further comprising a thermoplastic elastomer (D).

5. The resin composition according to claim 4, wherein the thermoplastic elastomer (D) contains at least one selected from the group consisting of: a core-shell structure polymer (d1) that has a core layer and a shell layer containing an alkyl (meth)acrylate polymer on a surface of the core layer; and an olefin polymer (d2) that is a polymer of an α-olefin and an alkyl (meth)acrylate and contains 60% by mass or more of a structural unit derived from the α-olefin.

6. The resin composition according to claim 1, wherein a mass percentage of the compound (C) based on a total amount of the cellulose acylate (A), the cardanol compound (B) and the compound (C) is from 0.1% by mass to 5% by mass.

7. The resin composition according to claim 1, wherein a content of the cellulose acylate (A) in the resin composition based on a total amount of the resin composition is 50% by mass or more.

8. The resin composition according to claim 1, wherein a content ratio of the cardanol compound (B) to the cellulose acylate (A) is 0.03≤(B)/(A)≤0.3.

9. A resin molded article comprising the resin composition according to claim 1.

10. The resin molded article according to claim 9, wherein the resin molded article is an injection molded article.

11. The resin composition according to claim 1, wherein said hindered phenol compound is chosen from pentaerythritol tetrakis(3-(3',5'-di-t-butyl-4'-hydroxyphenyl)propionate); ethylenebis(oxyethylene) bis(3-(3-tert-butyl-4-hydroxy-5-methylphenyl)propionate); 2,2'-dimethyl-2,2'-(2,4,8,10-tetraoxaspiro(5.5)undecane-3,9-diyl)dipropane-1,1'-diyl bis(3-(3-tert-butyl-4-hydroxy-5-methylphenyl) propanoate); 2-t-butyl-6-(3-t-butyl-2-hydroxy-5-methylbenzyl)-4-methylphenyl acrylate; 2-(1-(2-hydroxy-3,5-di-t-pentylphenyl)ethyl)-4,6-di-t-pentylphenyl acrylate; and combinations thereof.

12. The resin composition according to claim 1, wherein said phosphite compound is chosen from tris(2,4-di-t-butylphenyl) phosphite; 6-(3-(3-t-butyl-4-hydroxy-5-methylphenyl)propoxy)-2,4,8,10-tetra-t-butyl dibenzo(d,f)(1,3,2) dioxaphosphepin; and combinations thereof.

13. The resin composition according to claim 1, wherein the compound (C) comprises a combination of pentaerythritol tetrakis(3-(3',5'-di-t-butyl-4'-hydroxyphenyl)propionate) and tris(2,4-di-t-butylphenyl) phosphite.

14. The resin composition according to claim 1, wherein the compound (C) comprises a hindered phenol compound comprising at least one compound selected from the group consisting of a compound represented by a general formula (HP1) and a compound represented by a general formula (HP2),

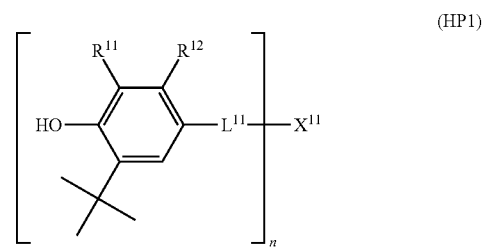
(HP1)

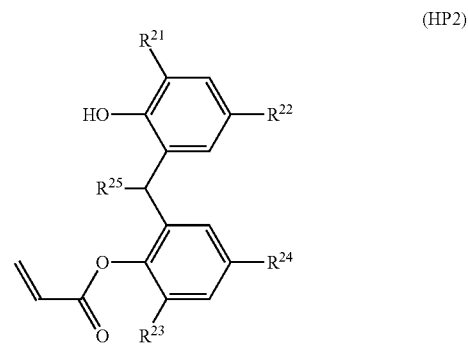
(HP2)

wherein $R^{11}$ and $R^{12}$ each independently represent a hydrogen atom or an alkyl group having 1 to 6 carbon atoms, $L^{11}$ represents a single bond or a divalent linking group, $X^{11}$ represents a single bond or an n-valent group, and n represents 1, 2, 3 or 4, and $R^{21}$, $R^{22}$, $R^{23}$, $R^{24}$, and $R^{25}$ each independently represent a hydrogen atom or an alkyl group having 1 to 6 carbon atoms.

15. The resin composition according to claim 1, wherein the compound (C) comprises a phosphite compound comprising at least one selected from the group consisting of a compound represented by a general formula (P1), a compound represented by a general formula (P2), and a compound represented by a general formula (P3),

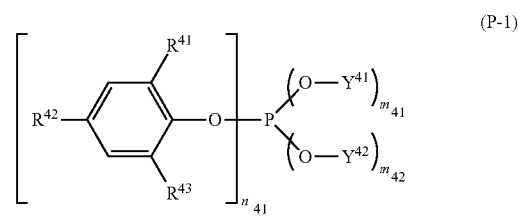
(P-1)

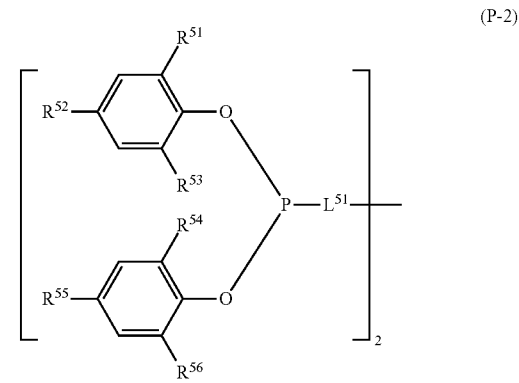
(P-2)

-continued

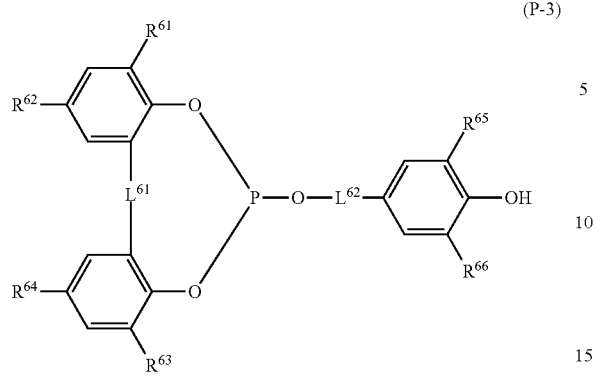

(P-3)

wherein $R^{41}$, $R^{42}$ and $R^{43}$ each independently represent a hydrogen atom or an alkyl group having 1 to 12 carbon atoms, $Y^{41}$ and $Y^{42}$ each independently represent an aliphatic hydrocarbon group, $n_{41}$ represents 1, 2 or 3, $m_{41}$ represents 0 or 1, m42 represents 0 or 1, and $n_{41}+m_{41}+m_{42}=3$, $R^{51}$, $R^{52}$, $R^{53}$, $R^{54}$, $R^{55}$, and $R^{56}$ each independently represent a hydrogen atom or an alkyl group having 1 to 12 carbon atoms, and $L^{51}$ represents a single bond or a divalent linking group and, $R^{61}$, $R^{62}$, $R^{63}$, $R^{64}$, $R^{65}$, and $R^{66}$ each independently represent a hydrogen atom or an alkyl group having 1 to 12 carbon atoms, and $L^{61}$ and $L^{62}$ each independently represent a single bond or a divalent linking group.

\* \* \* \* \*